US008545886B2

(12) United States Patent
Eisenreich et al.

(10) Patent No.: US 8,545,886 B2
(45) Date of Patent: Oct. 1, 2013

(54) EXTENDED RELEASE TABLET FORMULATIONS OF FLIBANSERIN AND METHOD FOR MANUFACTURING THE SAME

(75) Inventors: Wolfram Eisenreich, Ulm (DE); Thomas Friedl, Ochsenhausen (DE)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 958 days.

(21) Appl. No.: 11/837,957

(22) Filed: Aug. 13, 2007

(65) Prior Publication Data
US 2008/0038346 A1 Feb. 14, 2008

(30) Foreign Application Priority Data

Aug. 14, 2006 (EP) .................................... 06118896

(51) Int. Cl.
*A61K 9/22* (2006.01)
*A61K 9/52* (2006.01)
*A61K 9/26* (2006.01)
*A61K 9/14* (2006.01)
*A61K 31/497* (2006.01)
*A61K 31/50* (2006.01)
*A61P 25/24* (2006.01)
*C07D 403/00* (2006.01)
*C07D 235/00* (2006.01)
*C07D 235/04* (2006.01)
*C07D 235/24* (2006.01)

(52) U.S. Cl.
USPC ........... 424/468; 424/457; 424/470; 424/484; 424/485; 424/486; 424/487; 424/488; 514/17.6; 514/253.01; 544/295; 544/366; 544/370; 548/304.4; 548/304.7; 548/306.4

(58) Field of Classification Search
None
See application file for complete search history.

(56) References Cited

U.S. PATENT DOCUMENTS

| | | |
|---|---|---|
| 3,096,248 A | 7/1963 | Rudzki |
| 3,406,178 A | 10/1968 | Crocker et al. |
| 3,472,854 A | 10/1969 | Archer |
| 4,200,641 A | 4/1980 | Vandenberk et al. |
| 4,367,217 A | 1/1983 | Gruber et al. |
| 4,737,500 A | 4/1988 | Sorg |
| 4,792,452 A | 12/1988 | Howard et al. |
| 4,797,399 A | 1/1989 | Ueda et al. |
| 4,859,692 A | 8/1989 | Bernstein et al. |
| 4,886,803 A | 12/1989 | Sueda et al. |
| 4,940,793 A | 7/1990 | Botrè et al. |
| 4,954,503 A | 9/1990 | Strupczewski et al. |
| 4,968,508 A | 11/1990 | Oren et al. |
| 5,002,948 A | 3/1991 | Perregaard et al. |
| 5,036,088 A | 7/1991 | Kitaura et al. |
| 5,225,417 A | 7/1993 | Dappen et al. |
| 5,405,642 A | 4/1995 | Gilis et al. |
| 5,407,686 A | 4/1995 | Patel et al. |
| 5,434,156 A | 7/1995 | Björk et al. |
| 5,492,907 A | 2/1996 | Pickar et al. |
| 5,552,412 A | 9/1996 | Cameron et al. |
| 5,576,318 A | 11/1996 | Bietti et al. |
| 5,591,743 A | 1/1997 | Patoiseau et al. |
| 5,854,290 A | 12/1998 | Arnsten et al. |
| 5,883,094 A | 3/1999 | Fliri et al. |
| 5,916,916 A | 6/1999 | Hauser et al. |
| 5,929,054 A | 7/1999 | Baker et al. |
| 5,977,106 A | 11/1999 | Patoiseau et al. |
| 6,068,846 A | 5/2000 | Cho et al. |
| 6,083,947 A | 7/2000 | Granger et al. |
| 6,165,513 A | 12/2000 | Dansereau et al. |
| 6,187,340 B1 | 2/2001 | Fukuta et al. |
| 6,281,218 B1 | 8/2001 | Cereda et al. |
| 6,284,757 B1 | 9/2001 | Sanner |
| 6,346,548 B1 | 2/2002 | Miller et al. |
| 6,426,087 B1 | 7/2002 | Saslawski et al. |
| 6,482,841 B1 | 11/2002 | Letelier et al. |
| 6,521,623 B1 | 2/2003 | Cereda et al. |
| 6,586,435 B2 | 7/2003 | Cereda et al. |
| 6,627,646 B2 | 9/2003 | Bakale et al. |
| 6,680,071 B1 | 1/2004 | Johnson et al. |
| 7,151,103 B2 | 12/2006 | Borsini et al. |
| 7,183,410 B2 | 2/2007 | Bombarda et al. |
| 7,420,057 B2 | 9/2008 | Bombarda et al. |
| 2002/0001397 A1 | 1/2002 | Ishikawa et al. |

(Continued)

FOREIGN PATENT DOCUMENTS

| | | |
|---|---|---|
| BE | 904945 | 12/1986 |
| CA | 2455628 A1 | 2/2003 |

(Continued)

OTHER PUBLICATIONS

U.S. Appl. No. 12/280,804, filed Aug. 27, 2008, Ceci.
U.S. Appl. No. 12/306,946, filed Dec. 29, 2008, Becker.
U.S. Appl. No. 12/306,945, filed Dec. 29, 2008, Pyke.
U.S. Appl. No. 12/306,878, filed Dec. 29, 2008, Castrol et al.

(Continued)

*Primary Examiner* — Robert A Wax
*Assistant Examiner* — Jeffrey T Palenik
(74) *Attorney, Agent, or Firm* — Michael P. Morris; Timothy X. Witkowski

(57) ABSTRACT

The invention is directed to a Pharmaceutical extended release system, particularly for oral administration, of a pH-dependent water-soluble active substance, comprising or essentially consisting of
a) flibanserin or a pharmaceutically acceptable derivative thereof as active substance;
b) one or more pharmaceutically acceptable pH-dependent polymers;
c) one or more pharmaceutically acceptable pH-independent polymers;
d) one or more pharmaceutically acceptable acids; and
e) optionally one or more additives.
The present invention provides a release profile of flibanserin which is independent on the pH in the gastrointestinal tract when administered orally resulting in a significantly improved bioavailability.

22 Claims, 4 Drawing Sheets

(56) References Cited

U.S. PATENT DOCUMENTS

| | | |
|---|---|---|
| 2002/0010216 A1 | 1/2002 | Rogosky et al. |
| 2002/0044962 A1* | 4/2002 | Cherukuri et al. ............ 424/459 |
| 2002/0103208 A1 | 8/2002 | Cereda et al. |
| 2002/0151543 A1 | 10/2002 | Barberich et al. |
| 2003/0027823 A1 | 2/2003 | Cereda et al. |
| 2003/0060475 A1 | 3/2003 | Borsini |
| 2003/0083228 A1 | 5/2003 | Carpino et al. |
| 2003/0104980 A1 | 6/2003 | Borsini et al. |
| 2003/0119850 A1 | 6/2003 | Bombarda et al. |
| 2004/0023948 A1 | 2/2004 | Green et al. |
| 2004/0048877 A1 | 3/2004 | Friedl et al. |
| 2004/0116532 A1 | 6/2004 | Heacock et al. |
| 2004/0132697 A1 | 7/2004 | Thurlow et al. |
| 2004/0147581 A1 | 7/2004 | Taylor et al. |
| 2004/0180088 A1* | 9/2004 | Dudhara et al. ............ 424/471 |
| 2004/0180904 A1 | 9/2004 | Beck |
| 2004/0193452 A1 | 9/2004 | Berman |
| 2004/0235861 A1 | 11/2004 | Borsini |
| 2004/0258749 A1 | 12/2004 | Guldner et al. |
| 2005/0004105 A1 | 1/2005 | Leahy et al. |
| 2005/0037983 A1 | 2/2005 | Dinan et al. |
| 2005/0065158 A1 | 3/2005 | Naylor et al. |
| 2005/0095293 A1* | 5/2005 | Brauns et al. ................ 424/469 |
| 2005/0159430 A1 | 7/2005 | Bombarda et al. |
| 2005/0239798 A1 | 10/2005 | Pyke |
| 2005/0245539 A1* | 11/2005 | Mendla et al. ........... 514/254.06 |
| 2006/0014757 A1 | 1/2006 | Pyke |
| 2006/0025420 A1 | 2/2006 | Brauns et al. |
| 2006/0052391 A1 | 3/2006 | Dolsten |
| 2006/0099262 A1* | 5/2006 | Chow et al. .................. 424/472 |
| 2006/0160822 A1 | 7/2006 | Borsini |
| 2006/0199805 A1 | 9/2006 | Pyke et al. |
| 2006/0204486 A1 | 9/2006 | Pyke et al. |
| 2006/0211685 A1 | 9/2006 | Pyke et al. |
| 2006/0252773 A1 | 11/2006 | Ceci |
| 2006/0258640 A1 | 11/2006 | Ceci et al. |
| 2006/0264511 A1 | 11/2006 | Pyke |
| 2006/0264512 A1 | 11/2006 | Pyke |
| 2007/0032654 A1 | 2/2007 | Bombarda et al. |
| 2007/0032655 A1 | 2/2007 | Bombarda et al. |
| 2007/0072872 A1 | 3/2007 | Borsini |
| 2007/0105869 A1 | 5/2007 | Pollentier et al. |
| 2007/0123540 A1 | 5/2007 | Ceci |
| 2007/0196473 A1 | 8/2007 | Friedl et al. |
| 2007/0265276 A1 | 11/2007 | Pollentier et al. |
| 2008/0038347 A1 | 2/2008 | Eisenreich et al. |
| 2008/0069873 A1 | 3/2008 | Pearnchob et al. |
| 2008/0103155 A1 | 5/2008 | Mendla et al. |
| 2008/0119482 A1 | 5/2008 | Dolsten |
| 2008/0242678 A1 | 10/2008 | Ceci et al. |
| 2008/0242679 A1 | 10/2008 | Ceci |
| 2009/0023712 A1 | 1/2009 | Ferger et al. |
| 2009/0054458 A1 | 2/2009 | Bombarda et al. |
| 2009/0176698 A1 | 7/2009 | Baiker et al. |
| 2009/0239881 A1 | 9/2009 | Becker |
| 2009/0247546 A1 | 10/2009 | Ceci et al. |
| 2009/0312242 A1 | 12/2009 | Castrol et al. |
| 2009/0318469 A1 | 12/2009 | Pyke et al. |

FOREIGN PATENT DOCUMENTS

| | | |
|---|---|---|
| CL | 1033-1999 | 5/1999 |
| CL | 2394-1999 | 10/1999 |
| CL | 1491-2001 | 6/2001 |
| CL | 2833-2001 | 11/2001 |
| CL | 418-2002 | 3/2002 |
| CL | 1706-2002 | 7/2002 |
| CL | 1878-2002 | 8/2002 |
| CL | 2389-2002 | 10/2002 |
| CL | 1751-2004 | 7/2004 |
| CL | 911-2005 | 4/2005 |
| CN | 1571670 A | 1/2005 |
| CN | 1655789 A | 8/2005 |
| DE | 3620643 A1 | 1/1987 |
| DE | 10138273 A1 | 2/2003 |
| EP | 0200322 A1 | 11/1986 |
| EP | 0376607 A1 | 7/1990 |
| EP | 0497985 A1 | 8/1992 |
| EP | 0526434 B1 | 2/1993 |
| EP | 0705832 A1 | 4/1996 |
| EP | 0816356 A1 | 1/1998 |
| EP | 0982030 A2 | 3/2000 |
| EP | 1256343 A1 | 11/2002 |
| EP | 1285658 | 2/2003 |
| EP | 1285658 A2 | 2/2003 |
| EP | 1014985 | 5/2003 |
| EP | 1518858 A1 | 3/2005 |
| EP | 1674102 | 6/2006 |
| GB | 2023594 A | 1/1980 |
| IE | 1992/1340 | 10/1992 |
| IL | 159151 | 2/2003 |
| IL | 160389 | 2/2004 |
| JP | 8-143476 | 6/1996 |
| RU | 93014306 A | 3/1995 |
| WO | 9202215 A1 | 2/1992 |
| WO | 92/03167 A1 | 3/1992 |
| WO | 92/19606 A1 | 11/1992 |
| WO | 93/03016 A1 | 2/1993 |
| WO | 95/01965 A1 | 1/1995 |
| WO | 95/19978 A1 | 7/1995 |
| WO | 95/34555 A1 | 12/1995 |
| WO | 96/05834 A1 | 2/1996 |
| WO | 96/16949 A1 | 6/1996 |
| WO | 9819668 A1 | 5/1998 |
| WO | 98/33784 A1 | 8/1998 |
| WO | 9833784 A1 | 8/1998 |
| WO | 98/42344 A1 | 10/1998 |
| WO | 99/19302 A1 | 4/1999 |
| WO | 9959593 A1 | 5/1999 |
| WO | 99/59584 A1 | 11/1999 |
| WO | 00/24383 A1 | 5/2000 |
| WO | 00/28993 A1 | 5/2000 |
| WO | 00/63193 A1 | 10/2000 |
| WO | 00/64441 A2 | 11/2000 |
| WO | 00/67735 A2 | 11/2000 |
| WO | 01/00224 A1 | 1/2001 |
| WO | 01/12170 A2 | 2/2001 |
| WO | 01/21593 A1 | 3/2001 |
| WO | 02/00654 A1 | 1/2002 |
| WO | 02/24662 A1 | 3/2002 |
| WO | 02/41894 A2 | 5/2002 |
| WO | 02/072586 A1 | 9/2002 |
| WO | 02/079143 A1 | 10/2002 |
| WO | 03/007949 A1 | 1/2003 |
| WO | 03/011396 A2 | 2/2003 |
| WO | 03/013539 A1 | 2/2003 |
| WO | 03/014079 A1 | 2/2003 |
| WO | 03/035072 A1 | 5/2003 |
| WO | 03074032 A1 | 9/2003 |
| WO | 03/097058 A1 | 11/2003 |
| WO | 2004/041259 A1 | 5/2004 |
| WO | 2004/045509 A2 | 6/2004 |
| WO | 2004/069339 A1 | 8/2004 |
| WO | 2005/007166 A1 | 1/2005 |
| WO | 2005/044238 A1 | 5/2005 |
| WO | 2005/087207 A1 | 9/2005 |
| WO | 2005/102342 A1 | 11/2005 |
| WO | 2005/102343 A1 | 11/2005 |
| WO | 2006/010574 A1 | 2/2006 |
| WO | 2006/019715 A1 | 2/2006 |
| WO | 2006024471 A1 | 3/2006 |
| WO | 2006/096434 A2 | 9/2006 |
| WO | 2006/096435 A2 | 9/2006 |
| WO | 2006/125041 A1 | 11/2006 |
| WO | 2007/014929 A1 | 2/2007 |
| WO | 2007/048803 A1 | 5/2007 |
| WO | 2007048803 A1 | 5/2007 |
| WO | 2007090091 A2 | 8/2007 |
| WO | 2008006838 A1 | 1/2008 |
| WO | 2008019996 A2 | 2/2008 |
| WO | 2008116890 A2 | 10/2008 |

OTHER PUBLICATIONS

Alexander et al., J. of Am. Acad. of Nurse Practitioners, 2007, 19:152-163.

Guilleminault et al., Atypical Sexual Behavior During Sleep, Phycosomatic Med., 2002, 64:328-336.

Basson et al., Sexual psychophysiology and effects of sildenafil citrate in oestrogenised women with acquired genital arousal disorder and impaired orgasm: a randomised controlled trial, BJOG: an International Journal of Obstetrics and Gyn., Nov. 2003, 110:1014-1024.

Basson et al., Efficacy and Safety of Sildenafil Citrate in Women with Sexual Dysfunction Associated with Female Sexual Arousal Disorder, J Women's Health & Gender-Based Medicine, Nov. 4, 2002 11:367-77.

Black et al., Inappropriate sexual behaviors in dementia, J of Geriatric Psychiatry & Neurology, Sep. 2005, 18(3):155-162.

Clayton, Epidemiology and Neurobiology of Femal Sexual Dysfunction, J Sex Med., Nov. 4, 2007, Suppl 4:260-8.

Clayton et al., Burden of phase-specific sexual dysfunction with SSRIs, J Affect Disord., Mar. 2006, 91(1):27-32.

Clayton et al., Prevalence of Sexual Dysfunction Among Newer Antidepressants, J. Clin. Psychiatry, 2002, 63(4):357-366.

CMU Pharmaceutical polymorphism, http://www.andrew.cmu.edu/user/suter/polymorph.html, internet p. 1-3 (2002): obtained Feb. 11, 2009.

Sexual Dysfunction and Hypotestosteronemia in Patients With Obstructive Sleep Apnea Syndrome and Its Effects With CPAP Therapy, http:...clinicaltrials.gov/ct2/show/NCT00832065, obtained Apr. 1, 2009, 4pgs.

Doelker et al., Crystalline modifications and polymorphism changes during drug manufacturing, Annales Pharmaceutiques Francaises, 2002, 60(3):161-169.

Doelker et al., Physicochemical behavior or active substances. Consequences for the feasibility and stability of pharmaceutical forms, S.T.P. Pharma Pratiques, 1999, 9(5):399-409.

Engleson, Concise Encyclopedia Chemistry, 1993, pp. 872-873.

Giraldi et al., Physiology of Female Sexual Function. Animal Models, J Sex Med, 2004, 1(3):237-253.

Girgis et al., A double-blind trial of clomipramine in premature ejaculation, Andrologia, Jul.-Aug. 1982, 14(4):364-8.

Goldfischer et al., Selected 2008 Abstracts from the International Society for the Study of Women's Sexual Health, J. Sex. Med., 2008, 5(suppl. 3):159-160.

Goodman, An assessment of clomipramine (Anafranil) in the treatment of premature ejaculation, J Int Med Res., 1980; 8(Suppl 3):53-9.

Haensel et al., Fluoxetine and premature ejaculation: A double-blind, crossover, placebo-controlled study, J Clin Psychopharmacology, 1998, 18:72-77.

Haensel et al., Clomipramine and sexual function in men with premature ejaculation and controls, J Urology, Oct. 1996, 156(B193):1310-1315.

Jain et al., Polymorphism in Pharmacy, Indian Drugs, 1986, 23(6):315-329.

Kandeel et al., Male Sexual Function and its Disorders: Physiology, Pathophysiology, Clinical investigation, and Treatment, Endocrine Reviews, 2001, 22(3):342-388 at 370.

Kennedy et al., Antidepressant-Induced Sexual Dysfunction During Treatment with Moclobemide, Paroxetine, Sertraline, and Venlafaxine, J Clin Psychiatry, 2000; 61:276-81.

Kennedy et al., Sexual dysfunction before antidepressant therapy in major depression, J. Affective Disorders, 1999, 56:201-208.

Konarski et al., Effects of Acute Flibanserin on FDG-PET Brain Glucose Metabolism in Men with Major Depressive Disorder, Aug. 2008 Barcelona meeting of the European College of Nueropsychopharmacology, 3 pgs. (poster-abstract).

McKenna, Neural Circuitry Involved in Sexual Function, J Spinal Cord Med., 2001, 24:148-154.

McMahon et al., Efficacy of type-5 phosphodiesterase inhibitors in the drug treatment of premature ejaculation: a systematic review, BJU Int., 2006, 98:259-72.

Montejo-Gonzales et al., SSRI-induced sexual dysfunction: fluoxetine, paroxetine, sertraline, and fluvoxamine in a prospective, multicenter, and descriptive clinical study of 344 patients, J Sex Marital, 1997 Fall; 23(3):176-94.

Muzaffar et al., J. Pharmacy, 1979, 1(1):59-66.

Nurnberg et al., Sildenafil for Sexual Dysfunction in Women Taking Antidepressants, Am J Psychiatry, October—Letters to the Editor, 1999, 156(10):1664.

Nurnberg et al., Sildenafil Treatment of Women with Antidepressant-Associated Sexual Dysfunction, JAMA, Jul. 2008, 300(4):395-404.

Pfaus et al., What can animal models tell us about human sexual response?, Annu Rev Sex Res, 2003, 14:1-63.

Porter, Remingtons, 1990, Chpt 90, pp. 1666-1675.

Pryor et al., Efficacy and tolerability of dapoxetine in treatment of premature ejaculation: an integrated analysis of two double-blind, randomized controlled trials, Lancet, 2006, 368(9539):929-37.

Pyke et al., Flibanserin: A Novel Centrally Acting Agent that is not an Effective Antidepressant but has Potential to Treat Decreased Sexual Desire in Women, APA, May 2008, 1 pg. (accepted poster).

Pyke et al., Flibanserin: A Novel Centrally Acting Agent that is not an Effective Antidepressant but has Potential to Treat Decreased Sexual Desire in Women, APA, May 2008, 1 pg. (accepted abstract).

Rapkin, General Gynecology, 2007, 196:97-106.

Rendell et al., Sildenafil for Treatment of Erectile Dysfunction in Men with Diabetes, JAMA, 1999, 281:421-426.

Rosen et al., Effects of SSRIs on sexual function: a critical review, J Clin Psychopharmacol., Feb. 1999 19(1):67-85.

Rosen et al., PDE-5 inhibition and sexual response: Pharmacological mechanisms and clinical outcomes, Annual Review of Sex Res, 2002, pp. 36-88.

Rosen, Sexual pharmacology in the 21st century, J Gend Specif Med., Jul.-Aug. 2000, 3(5):45-52.

Rowland, Neurobiology of Sexual Response in Men and Women, 1:CNS Spectr., Aug. 2006, 11(8 Suppl 9):6-12.

Rubenstein, Pharmaceutics: The Science of Dosage Form Design, ed. Aulton, 1988, pp. 304-321.

Martin, Sexsomnia, http://lakesidepress.com/pulmonary/Sleep/sexsomnia.html, obtianed Apr. 1, 2009, 5pgs.

Stearns et al., J. of Clin. Oncology, 2002, 20(6):1436-1438.

Stedman'S Medical Dictionary definition "Prevention," 2000, 28th Ed., 3 pgs., Lippincott Williams & Wilkins.

Stoleru et al., Brain processing of visual sexual stimuli in men with hypoactive sexual desire disorder, Psychiatry Res.: Neuroimaging, 2003, 124(2):67-86.

Clayton et al., Validation of the Decreased Sexual Desire Screener (DSDS): a Brief Diagnostic Instrument for Generalized, Acquired Hypoactive Sexual Desire Disorder in Women, International Society for the Study of Womens Sexual Health (ISSWSH) annual meeting, 2007, 2 pgs. (poster and abstract).

Wunderlich et al., Using e-Diaries to Measure Sexual Desire in Women with Hypoactive Sexual Desire Disorder, International Society for the Study of Womens Sexual Health (ISSWSH) annual meeting, 2007, 11 pgs. (Oral Presentation).

Clayton et al., Validation of the Sexual Interest and Desire Inventory-Female (SIDI-F) in North American Women, International Society for the Study of Womens Sexual Health (ISSWSH) annual meeting, 2007, 3 pgs. (poster and abstract).

Clayton et al., Validity of Sexual Distress Scales vs Electronic Diary in Women with Decreased Sexual Desire , American College of Obstetrics and Gynecologists (ACOG) annual meeting, 2007, 1 pg. (abstract only).

Clayton et al., Validating the Sexual Interest and Desire Inventory (SIDI-F) in North American Women , American College of Obstetrics and Gynecologists (ACOG) annual meeting, 2007, 1 pg. (abstract only).

Clayton et al., Validation of the Sexual Interest and Desire Inventory-Female (SIDI-F) in North American Women, American Psychiatric Association (APA) annual meeting, 2007, 2 pgs. (poster and abstract).

Tignol et al., Using e-Diaries to Measure Sexual Desire in Women with Hypoactive Sexual Desire Disorder, European Society for Sexual Medicine (ESSM) annual meeting, 2007, 9 pgs. (oral presentation).

Clayton, Baseline characteristics of patients enrolled in three Phase III North American trials of flibanserin in premenopausal women with Hypoactive Sexual Desire Disorder, Joint Congress of the European and International Societies of Sexual Medicine (ESSM/ISSM) 2008, 10 pgs. (oral presentation).

Clayton et al., Baseline characteristics of patients enrolled in three Phase III North American trials of flibanserin in premenopausal women with Hypoactive Sexual Desire Disorder, Joint Congress of the European and International Societies of Sexual Medicine (ESSM/ISSM) 2008, 1 pgs. (abstract).

Clayton et al., Baseline characteristics of patients enrolled in three Phase III North American trials of flibanserin in premenopausal women with Hypoactive Sexual Desire Disorder, International Society for the Study of Womens Sexual Health (ISSWSH) annual meeting 2009, poster, 2 pgs. (poster and abstract).

Clayton et al., Validation of the Decreased Sexual Desire Screener (DSDS): A Brief Diagnostic Instrument for Generalized Acquired Female Hypoactive Sexual Desire Disorder (HSDD); J. Sex Med., 2009, pp. 1-9. (epub ahead of print).

Dean, Decreased Sexual Desire Screener© (DSDS©) for Diagnosis of Hypoactive Sexual Desire Disorder in Women, WONCA Europe conference, 2008, 8 pgs. (oral presentation).

Dean et al., Decreased Sexual Desire Screener© (DSDS©) for Diagnosis of Hypoactive Sexual Desire Disorder in Women, WONCA Europe conference, 2008, 1 pg. (abstract).

Derogatis et al., Validation of Sexual Distress Scales and Electronic Diary in Women with Hypoactive Sexual Desire Disorder, International Society for the Study of Womens Sexual Health (ISSWSH) annual meeting, 2007, 3 pgs. (poster and abstract).

Derogatis et al., Validation of Sexual Distress Scales and Electronic Diary in Women with Hypoactive Sexual Desire Disorder. American Psychiatric Association (APA) annual meeting, 2007, 2 pgs. (poster and abstract).

Derogatis et al., Content Validity of the Female Sexual Distress Scale-Revised (FSDS-R) in Women with Hypoactive Sexual Desire Disorder (HSDD), Joint Congress of the European and International Societies of Sexual Medicine (ESSM/ISSM) 2008, 5 pgs. (poster, oral presentation and abstract).

Derogatis et al., Validation of the Female Sexual Distress Scale Revised (FSDS-R) for assessing distress in women with Hypoactive Sexual Desire Disorder (HSDD), J Sex Med., 2008, 5:357-364.

Dennerstein et al., Differentiating Four Cognitive-Behavioral Types of Women with Low Sexual Desire, International Society for the Study of Womens Sexual Health (ISSWSH) annual meeting, 2007, 9 pgs. (Oral Presentation).

Dennerstein et al., Differentiating Four Cognitive-Behavioral Types of Women with Decreased Sexual Desire, International Society for the Study of Womens Sexual Health (ISSWSH) annual meeting, 2007, 2 pgs. (abstract).

Dennerstein et al., Differentiating Four Cognitive-Behavioral Types of Women with Decreased Sexual Desire, American Psychiatric Association (APA) annual meeting, 2007, 3 pgs. (poster and abstract).

Dennerstein et al., Differentiating Four Cognitive-Behavioral Types of Women with Decreased Sexual Desire, European Society for Sexual Medicine (ESSM) annual meeting, 2007, 3 pgs. (poster and abstract).

Dennerstein, Differentiating Four Cognitive-Behavioral Types of Women with Low Sexual Desire, European Society for Sexual Medicine (ESSM) annual meeting, 2007, 10 pgs. (oral presentation).

Dennerstein et al., Attitudes Towards Partner Interactions of Women With Characteristics of HSDD: Preliminary Results of a Multinational Study of 1,402 Women. International Society for the Study of Womens Sexual Health (ISSWSH) annual meeting, 2008, 12 pgs. (oral presentation and abstract).

Goldfischer et al., Validation of the Decreased Sexual Desire Screener (DSDS): a Brief Diagnostic Instrument for Generalized, Acquired Hypoactive Sexual Desire Disorder in Women, American Psychiatric Association (APA) annual meeting, 2007, 2 pgs. (poster and abstract).

Pyke et al., The Rose Study: Placebo-controlled Randomized Withdrawal Trial of Flibanserin for Hypoactive Sexual Desire Disorder in Premenopausal Women, Sexual Medicine Society of North America (SMSNA) annual meeting, 2007, 1 pg. (poster).

Goldfischer et al., Efficacy of Continued Flibanserin Treatment on Sexual Desire and Satisfying Sexual Events in Premenopausal Women With HSDD: Results From the ROSE Study, International Society for the Study of Womens Sexual Health (ISSWSH) annual meeting, 2008, 1 pgs. (abstract).

Goldfischer et al., Efficacy of Continued Flibanserin Treatment on Distress Associated with Sexual Dysfunction in Premenopausal Women With HSDD: Results From the ROSE Study, International Society for the Study of Womens Sexual Health (ISSWSH) annual meeting, 2008, 2 pgs. (poster and abstract).

Goldfischer et al., Efficacy of Continued Flibanserin Treatment on Sexual Functioning in Premenopausal Women With HSDD: Results From the ROSE Study, International Society for the Study of Womens Sexual Health (ISSWSH) annual meeting, 2008, oral presentation, 1 pg. (abstract only).

Goldfischer et al., The ROSE Study: Placebo-controlled Randomized Withdrawal Trial of Flibanserin for Hypoactive Sexual Desire Disorder in Premenopausal Women, European Board and College of Obstetrics and Gynaecology (EBCOG) annual meeting, 2008, 1 pg. (abstract only).

Goldfischer et al., The Rose Study: Placebo-controlled Randomized Withdrawal Trial of Flibanserin for Hypoactive Sexual Desire Disorder in Premenopausal Women. European Federation of Sexology (EFS), 2008, 7 pgs. (oral presentation and abstract).

Goldfischer et al., Decreased Sexual Desire Screener (DSDS) for Diagnosis of Hypoactive Sexual Desire Disorder in Women, American College of Obstetrics and Gynecologists (ACOG) annual meeting, 2008, 2 pgs. (poster and abstract).

Goldfischer et al., Efficacy of Continued Flibanserin Treatment in Premenopausal Women with Hypoactive Sexual Desire Disorder: Results from the ROSE Study, International Academy of Sex Research (IASR) annual meeting, 2008, 3 pgs. (poster and abstract).

Goldfischer et al., Safety and Tolerability of Flibanserin in Premenopausal Women with Hypoactive Sexual Desire Disorder: Results from the ROSE Study, International Academy of Sex Research (IASR) annual meeting, 2008, 3 pgs. (poster and abstract).

Goldfischer et al., Efficacy and Safety of Flibanserin in Premenopausal Women with Hypoactive Sexual Desire Disorder: Results from the Randomized Withdrawal ROSE Study, Institute on Psychiatric Services (IPS) annual meeting, 2008, 2 pgs. (poster and abstract).

Goldfischer et al., Decreased Sexual Desire Screener (DSDS) for Diagnosis of Hypoactive Sexual Desire Disorder in Women, Sexual Medicine Society of North America (SMSNA) annual meeting, 2008, 3 pgs. (poster and abstract).

Goldfischer et al., Efficacy and Safety of Flibanserin in Premenopausal Women with Hypoactive Sexual Desire Disorder: Results From the Randomized Withdrawal ROSE Study, Sexual Medicine Society of North America (SMSNA) annual meeting, 2008, 3 pgs. (poster and abstract).

Goldfischer, Efficacy of Continued Flibanserin Treatment in Premenopausal Women with Hypoactive Sexual Desire Disorder: Results From the ROSE Study, Joint Congress of the European and International Societies of Sexual Medicine (ESSM/ISSM), 2008, 10 pgs. (oral presentation).

Goldfischer et al., Efficacy of Continued Flibanserin Treatment in Premenopausal Women with Hypoactive Sexual Desire Disorder: Results From the ROSE Study, Joint Congress of the European and International Societies of Sexual Medicine (ESSM/ISSM), 2008, 2 pgs. (abstract).

Goldfischer et al., Safety and Tolerability of Continued Flibanserin Treatment in Premenopausal Women with Hypoactive Sexual Desire Disorder: Results From the ROSE Study, Joint Congress of the European and International Societies of Sexual Medicine (ESSM/ISSM), 2008, 2 pgs. (poster and abstract).

Goldstein et al., Differences in Patient-Physician Communication Regarding Hypoactive Sexual Desire Disorder (HSDD), Sexual Medicine Society of North America (SMSNA) annual meeting, 2007, 3 pgs. (poster and abstract).

Goldstein et al., Emotions Related to Distress in Patients with Hypoactive Sexual Desire Disorder: Results of Patient and Physician Interviews, Sexual Medicine Society of North America (SMSNA) annual meeting, 2007, 3 pgs. (poster and abstract).

Jolly et al., Design of Phase III Pivotal Trials of Flibanserin in Female Hypoactive Sexual Desire Disorder (HSDD), European Federation of Sexology (EFS), 2008, 2 pgs. (poster and abstract).
Nappi et al., Validation of the Sexual Interest and Desire Inventory-Female (SIDI-F) in European Women, European Federation of Sexology (EFS), 2008, 2 pgs. (poster and abstract).
Nappi, Decreased Sexual Desire Screener (DSDS) for Diagnosis of Hypoactive Sexual Desire Disorder (HSDD) in European Women, Joint Congress of the European and International Societies of Sexual Medicine (ESSM/ISSM), 2008, 8 pgs. (oral presentation).
Nappi et al., Decreased Sexual Desire Screener (DSDS) for Diagnosis of Hypoactive Sexual Desire Disorder (HSDD) in European Women, Joint Congress of the European and International Societies of Sexual Medicine (ESSM/ISSM), 2008, 1 pg. (abstract).
Nappi et al., Decreased Sexual Desire Screener (DSDS) for Diagnosis of Hypoactive Sexual Desire Disorder (HSDD) in European Women, International Society for the Study of Womens Sexual Health (ISSWSH) annual meeting, 2009, oral presentation, 8 pgs. (oral presentation).
Nappi et al., Decreased Sexual Desire Screener (DSDS) for Diagnosis of Hypoactive Sexual Desire Disorder (HSDD) in European Women, International Society for the Study of Womens Sexual Health (ISSWSH) annual meeting, 2009, oral presentation, 1 pg. (abstract).
Pyke et al., Using e-Diaries to Measure Sexual Desire in Women with Hypoactive Sexual Desire Disorder, American Psychiatric Association (APA) annual meeting, 2007, 2 pgs. (poster and abstract).
Pyke et al., The ROSE Study: Placebo-Controlled Randomized Withdrawal Trial of Flibanserin for Hypoactive Sexual Desire Disorder in Premenopausal Women (Study Design Only), Institute on Psychiatric Services (IPS) annual meeting, 2007, 2 pgs. (poster and abstract).
Pyke et al., Safety and Tolerability of Flibanserin in Premenopausal Women With Hypoactive Sexual Desire Disorder (HSDD): Results From the ROSE Study, American Psychiatric Association (APA) annual meeting, 2008, 2 pgs. (poster and abstract).
Pyke et al., Flibanserin: a Novel Centrally Acting Agent That is not an Effective Antidepressant but has Potential to Treat Decreased Sexual Desire in Women, American Psychiatric Association (APA) annual meeting, 2008, 2 pgs. (poster and abstract).
Rosen et al., The Predictors of Sexual Distress in Women With Low Sexual Desire, International Society for the Study of Womens Sexual Health (ISSWSH) annual meeting, 2009, oral presentation, 15 pgs. (oral presentation and abstract).
Shifren et al., Sexual Problems and Distress in United States Women: Prevalence and Correlates, Obstet. Gynecology, Nov. 2008, 112(5):970-978.
Shifren et al., Treatment-seeking Behavior of U.S. Women with Hypoactive Sexual Desire Disorder (HSDD), American College of Obstetrics and Gynecologists (ACOG) annual meeting, 2008, 2 pgs. (poster and abstract).
Pyke et al., Validation of the Sexual Interest and Desire Inventory-Female (SIDI-F) in European Women, International Society for the Study of Womens Sexual Health (ISSWSH) annual meeting, 2007, 20 pgs. (oral presentation).
Nappi et al., Validation of the Sexual Interest and Desire Inventory-Female (SIDI-F) in European Women, European Society for Sexual Medicine (ESSM) annual meeting, 2007, 19 pgs. (oral presentation).
Sand et al., The Female Sexual Function Index (FSFI): A Potential "Gold Standard" Measure for Assessing Therapeutically-Induced Change in Female Sexual Function, ASRM, 2009, Oct. 17-21, 2009, Atlanta, Georgia, 2 pgs. (poster and abstract).
Smith et al., Pharmacokinetics of Flibanserin in Premenopausal Women With Hypoactive Sexual Desire Disorder Including Effects on the Female Sexual Function Index, ESSM, 2009, Nov. 2009, 2 pgs., Lyon. (poster and abstract).
Clayton et al., Efficacy of Flibanserin as a Potential Treatment for Hypoactive Sexual Desire Disorder in North American Premenopausal Women: Results From the Dahlia Trial, ESSM, 2009, Nov. 2009, 2 pgs., Lyon. (poster and abstract).
Thorp et al., Efficacy of Flibanserin as a Potential Treatment for Hypoactive Sexual Desire Disorder in North American Premenopausal Women: Results From the Daisy Trial, ESSM, 2009, Nov. 2009, 3 pgs., Lyon. (poster and abstract).
Jolly et al., Design of Randomized Controlled Trials of Flibanserin in Premenopausal Women With Hypoactive Sexual Desire Disorder, ESSM 2009, Nov. 2009, 3 pgs., Lyon. (poster and abstract).
Revicki et al., Content Validity of the Female Sexual Function Index in Pre- and Postmenopausal Women With Hypoactive Sexual Desire Disorder, ESSM 2009, Nov. 2009, 2 pgs., Lyon. (poster and abstract).
Aubert et al., Comparison of Flibanserin With the 5-Ht1a Agonist (+)-8-Oh-Dpat in Affecting Interactions Between Male-Female Marmoset Pairs, ESSM 2009, Nov. 2009, 2 pgs., Lyon (poster and abstract).
Rosen et al., Criterion Validity of the Sexual Desire Domain of the Female Sexual Function Index (Fsfi): Identifying a Diagnostic Cut-Point for Differentiating Women With and Without Hsdd, ESSM 2009, Nov. 2009, 3 pgs., Lyon. (poster and abstract).
Rosen et al., Validation of the FSFI Sexual Desire Domain Diagnostic Cut-Point in Predicting Hsdd in Women: Independent Replication and Confirmation, ESSM 2009, Nov. 2009, 2 pgs., Lyon. (poster and abstract).
Nappi, Efficacy of Flibanserin As a Potential Treatment for Hypoactive Sexual Desire Disorder in European Premenopausal Women: Results From the Orchid Trial; ESSM 2009, Nov. 2009, 12 pgs., Lyon. (oral presentation).
Nappi et al., Efficacy of Flibanserin as a Potential Treatment for Hypoactive Sexual Desire Disorder in European Premenopausal Women: Results From the Orchid Trial; ESSM 2009, Nov. 2009, 1 pg., Lyon. (abstract).
Holstege et al., Differences in Brain Activity in Premenopausal Women With Hypoactive Sexual Desire Disorder (Hsdd) Compared to Women Without Sexual Dysfunction, ESSM 2009, Nov. 2009, 2 pgs., Lyon. (abstract only).
Holstege et al., Brain activation and de-activation caused by erotic movies is lower in HSDD- than in non-HSDD volunteers, ESSM 2009, 8 pgs. (oral presentation).
Jolly, Efficacy of Flibanserin 100 Mg Qhs as a Potential Treatment for Hypoactive Sexual Desire Disorder in Premenopausal Women, ESSM 2009, Nov. 2009, 12 pgs., Lyon. (oral presentation).
Jolly et al., Efficacy of Flibanserin 100 Mg Qhs as a Potential Treatment for Hypoactive Sexual Desire Disorder in Premenopausal Women, ESSM 2009, Nov. 2009, 1 pgs., Lyon. (abstract).
Jolly et al., Efficacy of Flibanserin 100 Mg Qhs as a Potential Treatment for Hypoactive Sexual Desire Disorder in North American Premenopausal Women, ESSM 2009, Nov. 2009, 2 pgs., Lyon. (poster and abstract).
Clayton, Safety and Tolerability of Flibanserin in Premenopausal Women With Hypoactive Sexual Desire Disorder, ESSM 2009, Nov. 2009, 12 pgs., Lyon. (oral presentation).
Jolly et al., Safety and Tolerability of Flibanserin in Premenopausal Women With Hypoactive Sexual Desire Disorder, ESSM 2009, Nov. 2009, 1 pg., Lyon. (abstract).
Jolly et al., Efficacy of Flibanserin as a Potential Treatment for Hypoactive Sexual Desire Disorder in North American Premenopausal Women: Results From the Violet Trial, ESSM 2009, Nov. 2009, 3 pgs., Lyon. (poster and abstract).
Fuchs, Baseline Characteristics of Patients Enrolled in Three Phase III North American Trials of Flibanserin in Premenopausal Women With Hypoactive Sexual Desire Disorder, FIGO 2009, Oct. 2009, 10 pgs., Cape Town, South Africa. (oral presentation).
Goldfischer, Efficacy and Safety of Flibanserin in a Randomized Withdrawal Study of Premenopausal Women With Hypoactive Sexual Desire Disorder, FIGO2009, Oct. 2009, 12 pgs., Cape Town, South Africa. (oral presentation).
Goldfischer et al., Efficacy and Safety of Flibanserin in a Randomized Withdrawal Study of Premenopausal Women With Hypoactive Sexual Desire Disorder, FIGO2009, Oct. 2009, 1 pgs., Cape Town, South Africa. (abstract).
Revicki et al., Content Validity of the Female Sexual Function Index in Pre- and Postmenopausal Women With Hypoactive Sexual Desire Disorder, ICSM 2009, Jul. 2009, 2 pgs., Paris. (poster and abstract).
Revicki et al., Content Validity of the Female Sexual Function Index in Pre-Menopausal Women With Hypoactive Sexual Desire Disorder, ICSM 2009, Jul. 2009, 2 pgs., Paris. (poster and abstract).

Rosen et al., Criterion Validity of the Sexual Desire Domain of the Female Sexual Function Index (Fsfi): Identifying a Diagnostic Cut-Point for Differentiating Women With and Without Hsdd, ICSM 2009, Jul. 2009, 2 pgs., Paris. (poster and abstract).

Rosen et al., Validation of the Fsfi Sexual Desire Domain Diagnostic Cut-Point in Predicting Hsdd: Independent Replication and Confirmation, ICSM 2009, Jul. 2009, 2 pgs., Paris. (poster and abstract).

Sand et al., The Female Sexual Function Index (Fsfi): A Potential "Gold Standard" Measure for Assessing Sexual Function in Women, ICSM 2009, Jul. 2009, 2 pgs., Paris. (poster and abstract).

Jayne, Results From the Dahlia (511.70) Trial: A Prospective Study of Flibanserin for the Treatment of Hypoactive Sexual Desire Disorder in North American Premenopausal Women, SMSNA 2009, Nov. 2009, 3 pgs,, San Diego, USA (oral presentation).

Jayne et al., Results From the Dahlia (511.70) Trial: A Prospective Study of Flibanserin for the Treatment of Hypoactive Sexual Desire Disorder in North American Premenopausal Women, SMSNA 2009, Nov. 2009, 2 pgs., San Diego, USA (abstract and poster).

Sand et al., Efficacy of Flibanserin in North American Premenopausal Women With Hypoactive Sexual Desire Disorder: Results From the Daisy Trial, SMSNA 2009, Nov. 2009, 2 pgs., San Diego, USA. (poster and abstract).

Sand, Efficacy of Flibanserin in North American Premenopausal Women With Hypoactive Sexual Desire Disorder: Results From the Daisy Trial, SMSNA 2009, Nov. 2009, 2 pgs., San Diego, USA. (oral presentation).

Sand et al., The Female Sexual Function Index (Fsfi) is a Potential "Gold Standard" Measure for Assessing Sexual Function in Pre- and Post-Menopausal Women: A Systematic Review, SMSNA 2009, Nov. 2009, 2 pgs., San Diego, USA. (poster and abstract).

Sand et al., Efficacy of Flibanserin 100 Mg Qhs as a Potential Treatment for Hypoactive Sexual Desire Disorder in North American Premenopausal Women, SMSNA 2009, Nov. 2009, 2 pgs., San Diego, USA. (poster and abstract).

Sand, Efficacy of Flibanserin 100 Mg Qhs as a Potential Treatment for Hypoactive Sexual Desire Disorder in North American Premenopausal Women, SMSNA 2009, Nov. 2009, 2 pgs., San Diego, USA. (oral presentation).

Holstege et al., Differences in Brain Activity in Premenopausal Women With Hypoactive Sexual Desire Disorder (Hsdd) Compared to Women Without Sexual Dysfunction, SMSNA 2009, Nov. 2009, 2 pgs., San Diego, USA (abstract only).

Holstege et al., Brain activation and de-activation caused by erotic movies is lower in HSDD—than in non-HSDD volunteers, SMSNA, 2009, 4 pgs (poster & oral presentation).

Sand et al., Pooled Clinical Trail Analysis of Flibanserin Safety and Tolerability in Premenopausal Women with Hypoactive Sexual Desire Disorder, SMSNA, 2009, 2 pgs. (poster and abstract).

Sand, Pooled Clinical Trail Analysis of Flibanserin Safety and Tolerability in Premenopausal Women with Hypoactive Sexual Desire Disorder, SMSNA, 2009, 2 pgs. (oral presentation).

Sand et al., Effacacy of Flibanserin in North American Premenopausal Women with Hypoactive Sexual Desire Disorder: Results from the Violet Trial, SMSNA, 2009, 3 pgs. (poster and abstract).

Sand, Effacacy of Flibanserin in North American Premenopausal Women with Hypoactive Sexual Desire Disorder: Results from the Violet Trial, SMSNA, 2009, 2 pgs. (oral presentation).

Meston, The Female Sexual Function Index (FSFI) is a Potential "Gold Standard" Measure for Assessing Sexual Function in Pre- and post-menopausal Women: A Systematic Review, SMSNA, 2009, 3 pgs. (oral presentation).

Goldfischer, Efficacy and Safety of Flibanserin in a Randomized Withdrawal Study of Premenopausal Women With Hypoactive Sexual Desire Disorder, WAS, 2009, 12 pgs. (oral presentation).

Goldfischer et al., Efficacy and Safety of Flibanserin in a Randomized Withdrawal Study of Premenopausal Women With Hypoactive Sexual Desire Disorder, WAS, 2009, 1 pgs. (abst.).

Clayton et al., Baseline Characteristics of Patients Enrolled in Three Phase III North American Trials of Flibanserin in Premenopausaul Women with Hypoactive Sexual Desire Disorder, WAS, 2009, 2 pgs. (poster and abstract).

Clayton, Baseline Characteristics of Patients Enrolled in Three Phase III North American Trials of Flibanserin in Premenopausaul Women with Hypoactive Sexual Desire Disorder, WAS, 2009, 4 pgs. (oral presentation).

Derogatis et al., Content Validity of the Female Sexual Distress Scale-Revised in Women With Hypoactive Sexual Desire Disorder, WAS, 2009, 1 pg. (abstract only).

Dennerstein et al., Attitudes Toward and Frequency of Partner Interactions Among Women Reporting Decreased Sexual Desire, J. Sex Med., 2009, 6:1668-1673.

Goldstein et al., National Differences in Patient-Clinician Communication Regarding Hypoactive Sexual Desire Disorder, J. Sex Med., 2009, 6:1349-1357.

Johannes et al., Distressing Sexual Problems in United States Women Revisited: Prevalence After Accounting for Depression, J. Clin. Psych., 2009, 70(12):1698-1706.

Pfaus, Pathways of Sexual Desire, J. Sex Med., 2009, 6:1506-1533.

Rosen et al., Correlates of Sexually Related Personal Distress in Women with Low Sexual Desire, J. Sex Med., 2009, 6:1549-1560.

Lewis-D' Agostino et al., Validating the Sexual Interest and Desire Inventory (SIDI-F) in North American Women , American College of Obstetrics and Gynecologists (ACOG) annual meeting, 2007, 1 pg. (poster).

Shifren et al., Help-Seeking Behavior of Women with Self-Reported Distressing Sexual Problems, J. Of Women's Health, 2009, 18(4):461-468.

Wunderlich et al., Validity of Sexual Distress Scales vs Electronic Diary in Women with Decreased Sexual Desire , American College of Obstetrics and Gynecologists (ACOG) annual meeting, 2007, 1 pg. (poster).

Clayton et al., Using e-Diaries to Measure Sexual Desire in Women with Hypoactive Sexual Desire Disorder, European Society for Sexual Medicine (ESSM) annual meeting, 2007, 2 pgs. (abstract).

Van Lunsen et al., Validation of the Sexual Interest and Desire Inventory-Female (SIDI-F) in European Women, European Society for Sexual Medicine (ESSM) annual meeting, 2007, 1 pg. (abstract).

Clayton et al., Using e-Diaries to Measure Sexual Desire in Women with Hypoactive Sexual Desire Disorder, International Society for the Study of Womens Sexual Health (ISSWSH) annual meeting, 2007, 2 pgs. (abstract).

Van Lundsen, Validation of the Sexual Interest and Desire Inventory-Female (SIDI-F) in European women, ISSWSH, 2007, 2 pgs. (abstract).

Goldfischer et al., The ROSE Study: Placebo-controlled Randomized Withdrawal Trial of Flibanserin for Hypoactive Sexual Desire Disorder in Premenopausal Women, Sexual Medicine Society of North America (SMSNA) annual meeting, 2007, 1 pg. (abstract).

Krychman et al., The ROSE Study: Placebo-controlled Randomized Withdrawal Trial of Flibanserin for Hypoactive Sexual Desire Disorder in Premenopausal Women, European Board and College of Obstetrics and Gynaecology (EBCOG) annual meeting, 2008, 6 pgs. (poster and oral presentation).

Clayton et al., Baseline Characteristics of Patients Enrolled in Three Phase III North American Trials of Flibanserin in Premenopausal Women With Hypoactive Sexual Desire Disorder, FIGO 2009, Oct. 2009, 1 pg., Cape Town, South Africa. (abstract).

Scandroglio et al., Ex Vivo binding of Flibanserin to Serotonin-5-HT1A and 5-HT2A Receptors, Pharm. Res., 2001, 43(2):179-183.

D'Aquila et al., Anti-anhedonic actions of the novel serotonergic agent flibanserin, a potential rapidly-acting antidepressant, Euro. J. Pharm., 1997, 340:121-132.

Flik et al., Assessment of serotonin and catecholamine levels in the female rat brain following acute and chronic administration with flibanserin, a potential novel treatment for hypoactive sexual desire disorder: An in vivo microdialysis study, presented at Neuroscience 2009, Feb. 3, 2010, http://www.abstractsonline.com/Plan/AbstractPrintView.aspx?mID=2285&sKey=65206 . . . , 2 pgs.

Banfi et al., Benzimidazolone Derivatives: a new class of putative antidepressant agents, 13th Int. Symp. on Medicinal Chemistry, Sep. 19-23, 1994, p. 102. (abstract).

Borsini et la., BIMT 17, a 5-HT1A receptor agonist/5-HT2A receptor antagonist, directly activates portsynaptic 5-HT inhibitory responses in the rat cerebral cortex, Naunyn-Schmiedeberg's Arch Pharm., 1995, 352:283-290.

Boehringer Ingelheim, Flibanserin BIMT-17, Drugs of the Future, 1999, 24(1):91.

Podhorna et al., Flibanserin has anxiolytic effects without locomotor side effects in the infant rat ultrasonic vocalization model of anxiety, Workshop on Depression Anxiety Spectrum Disorders: from Neurobiology to Novel Pharm. Treatmts, Int. Acad. for Biomed. and Drug Res., Abstract-Book, Milan, Sep. 6-7, 2000, 1 pg.

Vaccarino et al., Flibanserin, a 5-HT1A agonist/5-HT2A antagonist, decreases sucrose intake in operant and non-operant paradigms in rats, Soc. Neurosci. Abstr., 2000, 26:394:Abstr 144.9, 30th Ann. Mtg. of Soc. for Neurosci, New Orleans, Nov. 4-9, 1000, 1 pg.

Borsini et al., Further characterisation of potential antidepressant action of flibanserin, Psychopharm., 2001, 159:64-69.

Rueter et al., In Vivo Electrophysiological Assessment of the Agonistic Properties of Flibanserin at Pre- and Postsynaptic 5-HT1A Receptors in the Rat Brain, Synapse, 1998, 29:392-405.

Cervo et al., Involvement of 5-HT1A receptors in flibanserin discriminative stimulus in female rats, Neurosci 2009, Feb. 3, 2010, http://www.abstractsonline.com/Plan/AbstratPrintView.aspx?mID=2285&sKey=65206 . . . , 2pgs.

Cervo et al., Involvement of 5-HT1A receptors in flibanserin discriminative stimulus in female rats, Dept. CNS Diseases, Prog. No. 465.20, 2009 Neurosci., Oct. 19, 2009, 1 pg. (poster).

Ferger et al., Neurochemical characterization of Flibanserin a phase III drug for treatment of hypoactive sexual desire disorder (HSDD) in women, Neurosci 2009, Feb. 3, 2010, http://www.abstractsonline.com/Plan/AbstractPrintView.aspx?mIK=2285&sKey=65206 . . . , 2pgs.

Flik et al., Assessment of serotonin and catecholamine levels in the female rat brain following acute and chronic administration with flibanserin, a potential novel treatment for hypoactive sexual desire disorder: An in vivo microdialysis study, SFN, 2009, 1 pg. (poster).

Ferger et al., Neurochemical characterization of Flibanserin a phase III drug for treatment of hypoactive sexual desire disorder (HSDD) in women, SFN, 2009, 1 pg. (poster).

Evans et al., The Effects of Flibanserin on Amphetamine Withdrawal-Induced hypolocomotion in Rats, Soc. Neurosci Abstr., Nov 7-12, 1998, 24:2133:Abstr 848.5, 28th Ann. Mtg. of the Soc. For Neurosci, Los Angeles, 1 pg.

Advisory Action dated Dec. 27, 2005, U.S. Appl. No. 10/272,603, filed Oct. 16, 2002 now US Pat. No. 7151103, issued Dec. 19, 2006, 3 pgs.

Examiner's Interview dated Jun. 23, 2006, U.S. Appl. No. 10/272,603, filed Oct. 16, 2002 now US Pat. No. 7151103, issued Dec. 19, 2006, 2 pgs.

Examiner's Interview dated Oct. 20, 2005, U.S. Appl. No. 10/272,603, filed Oct. 16, 2002 now US Pat. No. 7151103, issued Dec. 19, 2006, 1 pg.

Final Office Action dated Jun. 2, 2005, U.S. Appl. No. 10/272,603, filed Oct. 16, 2002 now US Pat. No. 7151103, issued Dec. 19, 2006, 9 pgs.

Notice of Allowance dated Jun. 23, 2006, U.S. Appl. No. 10/272,603, filed Oct. 16, 2002 now US Pat. No. 7151103, issued Dec. 19, 2006, 7 pgs.

Notice of Appeal/Amendment dated Nov. 8, 2005, U.S. Appl. No. 10/272,603, filed Oct. 16, 2002 now US Pat. No. 7151103, issued Dec. 19, 2006, 9 pgs.

Office Action dated Oct. 14, 2004, U.S. Appl. No. 10/272,603, filed Oct. 16, 2002 now US Pat. No. 7151103, issued Dec. 19, 2006, 8 pgs.

RCE/Supp. Amendment dated Jun. 8, 2006, U.S. Appl. No. 10/272,603, filed Oct. 16, 2002 now US Pat. No. 7151103, issued Dec. 19, 2006, 29 pgs.

Reply dated Feb. 14, 2005, U.S. Appl. No. 10/272,603, filed Oct. 16, 2002 now US Pat. No. 7151103, issued Dec. 19, 2006, 20 pgs.

Examiner's Search Strategy dated Jun. 20, 2006, U.S. Appl. No. 10/272,603, filed Oct. 16, 2002 now US Pat. No. 7151103, issued Dec. 19, 2006, 2 pgs.

Examiner's Search Strategy dated Jun. 21, 2006, U.S. Appl. No. 10/272,603, filed Oct. 16, 2002 now US Pat. No. 7151103, issued Dec. 19, 2006, 20 pgs.

Examiner's Search Strategy dated Sep. 22, 2004, U.S. Appl. No. 10/272,603, filed Oct. 16, 2002 now US Pat. No. 7151103, issued Dec. 19, 2006, 83 pgs.

Examiner's Search Strategy dated Sep. 28, 2004, U.S. Appl. No. 10/272,603, filed Oct. 16, 2002 now US Pat. No. 7151103, issued Dec. 19, 2006, 117 pgs.

Examiner's Search Strategy dated Sep. 29, 2004, U.S. Appl. No. 10/272,603, filed Oct. 16, 2002 now US Pat. No. 7151103, issued Dec. 19, 2006, 1 pg.

Examiner's Search Strategy dated Oct. 14, 2004, U.S. Appl. No. 10/272,603, filed Oct. 16, 2002 now US Pat. No. 7151103, issued Dec. 19, 2006, 3pgs.

Final Office Action dated Oct. 5, 2005, U.S. Appl. No. 10/210,474, filed Aug. 1, 2002 now US Pat. No. 7183410, issued Feb. 27, 2007, 6 pgs.

Notice of Allowance dated Jan. 30, 2006, U.S. Appl. No. 10/210,474, filed Aug. 1, 2002 now US Pat. No. 7183410, issued Feb. 27, 2007, 7 pgs.

Notice of Allowance dated Jul. 12, 2006, U.S. Appl. No. 10/210,474, filed Aug. 1, 2002 now US Pat. No. 7183410, issued Feb. 27, 2007, 7 pgs.

Office Action dated Mar. 16, 2005, U.S. Appl. No. 10/210,474, filed Aug. 1, 2002 now US Pat. No. 7183410, issued Feb. 27, 2007, 9 pgs.

Office Action dated Jul. 26, 2004, U.S. Appl. No. 10/210,474, filed Aug. 1, 2002 now US Pat. No. 7183410, issued Feb. 27, 2007, 7 pgs.

Response to Final Office Action dated Dec. 15, 2005, U.S. Appl. No. 10/210,474, filed Aug. 1, 2002 now US Pat. No. 7183410, issued Feb. 27, 2007, 9 pgs.

Reply dated Jan. 26, 2005, U.S. Appl. No. 10/210,474, filed Aug. 1, 2002 now US Pat. No. 7183410, issued Feb. 27, 2007, 24 pgs.

Amendment dated July, 11, 2005, U.S. Appl. No. 10/210,474, filed Aug. 1, 2002 now US Pat. No. 7183410, issued Feb. 27, 2007, 13 pgs.

Examiner's Search Strategy dated Mar. 10, 2005, U.S. Appl. No. 10/210,474, filed Aug. 1, 2002 now US Pat. No. 7183410, issued Feb. 27, 2007, 36 pgs.

Examiner's Search Strategy dated Sep. 30, 2005, U.S. Appl. No. 10/210,474, filed Aug. 1, 2002 now US Pat. No. 7183410, issued Feb. 27, 2007, 6 pgs.

Reply with Amendment dated Mar. 8, 2005, U.S. Appl. No. 10/210,474, filed Aug. 1, 2002 now US Pat. No. 7183410, issued Feb. 27, 2007, 10 pgs.

Supplemental Amendment dated Jan. 19, 2006, U.S. Appl. No. 10/210,474, filed Aug. 1, 2002 now US Pat. No. 7183410, issued Feb. 27, 2007, 6 pgs.

Examiner's Interview dated Nov. 19, 2007, U.S. Appl. No. 11/546,303, filed Oct. 12, 2006, 3 pgs.

Final Office Action dated Sep. 14, 2007, U.S. Appl. No. 11/546,303, filed Oct. 12, 2006, 4 pgs.

Office Action dated Jan. 5, 2007, U.S. Appl. No. 11/546,303, filed Oct. 12, 2006, 7 pgs.

Response dated Jul. 5, 2007, U.S. Appl. No. 11/546,303, filed Oct. 12, 2006, 6 pgs.

Examiner's Search Strategy dated Mar. 10, 2005, U.S. Appl. No. 11/546,303, filed Oct. 12, 2006, 36 pgs.

Examiner's Interview Summ. Dated Jan. 17, 2008, U.S. Appl. No. 11/546,304, filed Oct. 12, 2006 now US Pat No. 7420057 issued Sep. 2, 2008, 3 pgs.

Notice of Allowance dated Apr. 30, 2008, U.S. Appl. No. 11/546,304, filed Oct. 12, 2006 now US Pat No. 7420057 issued Sep. 2, 2008, 8 pgs.

Office Action dated Jan. 3, 2007, U.S. Appl. No. 11/546,304, filed Oct. 12, 2006 now US Pat No. 7420057 issued Sep. 2, 2008, 7 pgs.

Office Action dated Jul. 18, 2007, U.S. Appl. No. 11/546,304, filed Oct. 12, 2006 now US Pat No. 7420057 issued Sep. 2, 2008, 4 pgs.

Response dated Jan. 17, 2008, U.S. Appl. No. 11/546,304, filed Oct. 12, 2006 now US Pat No. 7420057 issued Sep. 2, 2008, 24 pgs.

Response dated Apr. 3, 2007, U.S. Appl. No. 11/546,304, filed Oct. 12, 2006 now US Pat No. 7420057 issued Sep. 2, 2008, 7 pgs.

Supp. Response dated Mar. 19, 2008, U.S. Appl. No. 11/546,304, filed Oct. 12, 2006 now US Pat No. 7420057 issued Sep. 2, 2008, 13 pgs.
Supp. Response dated Mar. 24, 2008, U.S. Appl. No. 11/546,304, filed Oct. 12, 2006 now US Pat No. 7420057 issued Sep. 2, 2008, 14 pgs.
2nd Supp. Response dated Apr. 23, 2008, U.S. Appl. No. 11/546,304, filed Oct. 12, 2006 now US Pat No. 7420057 issued Sep. 2, 2008, 14 pgs.
Final Office Action dated Apr. 23, 2007, U.S. Appl. No. 11/079,070, filed Mar. 14, 2005, 11 pgs.
Notice of Allowance dated Sep. 14, 2007, U.S. Appl. No. 11/079,070, filed Mar. 14, 2005, 6 pgs.
Office Action dated Jan. 11, 2008, U.S. Appl. No. 11/079,070, filed Mar. 14, 2005, 8 pgs.
Office Action dated Sep. 13, 2006, U.S. Appl. No. 11/079,070, filed Mar. 14, 2005, 5 pgs.
Response to Final Office Action dated Jul. 23, 2007, U.S. Appl. No. 11/079,070, filed Mar. 14, 2005, 7 pgs.
RCE dated Nov. 2, 2007, U.S. Appl. No. 11/079,070, filed Mar. 14, 2005, 4 pgs.
Response dated Jan. 16, 2007, U.S. Appl. No. 11/079,070, filed Mar. 14, 2005, 8 pgs.
Examiner Search Strategy dated Jan. 3, 2008, U.S. Appl. No. 11/079,070, filed Mar. 14, 2005, 20 pgs.
Examiner's Search Strategy dated Jul. 21, 2006, U.S. Appl. No. 11/079,070, filed Mar. 14, 2005, 106 pgs.
Advisory Action dated Jul. 2, 2009, U.S. Appl. No. 11/278,551, filed Apr. 4, 2006, 3 pgs.
Final Office Action dated Apr. 13, 2009, U.S. Appl. No. 11/278,551, filed Apr. 4, 2006, 9 pgs.
Office Action dated Jun. 1, 2007, U.S. Appl. No. 11/278,551, filed Apr. 4, 2006, 9 pgs.
Office Action dated Jul. 6, 2006, U.S. Appl. No. 11/278,551, filed Apr. 4, 2006, 8 pgs.
Office Action dated Jul. 9, 2008, U.S. Appl. No. 11/278,551, filed Apr. 4, 2006, 12 pgs.
Office Action dated Dec. 28, 2009, U.S. Appl. No. 11/278,551, filed Apr. 4, 2006, 9 pgs.
Responsive Amendment to Final Office Action, dated Jun. 12, 2009, U.S. Appl. No. 11/278,551, filed Apr. 4, 2006, 63 pgs.
RCE and Responsive Amendment to Final Office Action, dated Oct. 7, 2009, U.S. Appl. No. 11/278,551, filed Apr. 4, 2006, 14 pgs.
Response dated Jan. 9, 2009, U.S. Appl. No. 11/278,551, filed Apr. 4, 2006, 64 pgs.
Response dated Nov. 30, 2007, U.S. Appl. No. 11/278,551, filed Apr. 4, 2006, 25 pgs.
Response dated Dec. 19, 2006, U.S. Appl. No. 11/278,551, filed Apr. 4, 2006, 4 pgs.
Examiner's Search Strategy dated Apr. 13, 2009, U.S. Appl. No. 11/278,551, filed Apr. 4, 2006, 2 pgs.
Examiner's Search Strategy dated Jun. 1, 2007, U.S. Appl. No. 11/278,551, filed Apr. 4, 2006, 10 pgs.
Examiner's Search Strategy dated Jun. 26, 2006, U.S. Appl. No. 11/278,551, filed Apr. 4, 2006, 19 pgs.
Examiner's Search Strategy dated Jul. 9, 2008, U.S. Appl. No. 11/278,551, filed Apr. 4, 2006, 6 pgs.
Examiner's Search Strategy dated Dec. 28, 2009, U.S. Appl. No. 11/278,551, filed Apr. 4, 2006, 3 pgs.
Final Office Action dated Sep. 12, 2008, U.S. Appl. No. 11/381,590, filed Apr. 4, 2006, 10 pgs.
Office Action dated Apr. 3, 2007, U.S. Appl. No. 11/381,590, filed Apr. 4, 2006, 8 pgs.
Office Action dated Dec. 27, 2007, U.S. Appl. No. 11/381,590, filed Apr. 4, 2006, 8 pgs.
Response dated Jun. 26, 2008, U.S. Appl. No. 11/381,590, filed Apr. 4, 2006, 7 pgs.
Amendment and Reply dated Oct. 3, 2007, U.S. Appl. No. 11/381,590, filed Apr. 4, 2006, 8 pgs.
Examiner's Search Strategy dated Mar. 30, 2007, U.S. Appl. No. 11/381,590, filed Apr. 4, 2006, 48 pgs.
Office Action dated Mar. 23, 2009, U.S. Appl. No. 11/383,796, filed May 17, 2006; 11 pgs.
Examiner's Search Strategy dated Mar. 23, 2009, U.S. Appl. No. 11/383,796, filed May 17, 2006; 2 pgs.
Office Action dated Mar. 19, 2009, U.S. Appl. No. 11/383,793, filed May 17, 2006, 12 pgs.
Examiner's Search Strategy dated Mar. 19, 2009, U.S. Appl. No. 11/383,793, filed May 17, 2006, 3 pgs.
Advisory Action dated Feb. 10, 2009, U.S. Appl. No. 11/381,130, filed May 2, 2006, 3 pgs.
Final Office Action dated Jul. 18, 2008, U.S. Appl. No. 11/381,130, filed May 2, 2006, 17pgs.
Office Action dated Oct. 9, 2007, U.S. Appl. No. 11/381,130, filed May 2, 2006, 13 pgs.
Response to Final Office Action dated Jan. 21, 2009, U.S. Appl. No. 11/381,130, filed May 2, 2006, 13 pgs.
Response dated Apr. 9, 2008, U.S. Appl. No. 11/381,130, filed May 2, 2006, 36 pgs.
Office Action dated Jun. 1, 2009, U.S. Appl. No. 11/364,306, filed Feb. 28, 2006, 18 pgs.
Examiner's Search Strategy dated Jun. 1, 2009, U.S. Appl. No. 11/364,306, 3 pgs.
Final Office Action dated Sep. 4, 2008, U.S. Appl. No. 11/364,153, filed Feb. 28, 2006, 12 pgs.
Office Action dated Nov. 29, 2007, U.S. Appl. No. 11/364,153, filed Feb. 28, 2006, 11 pgs.
Response dated May 29, 2008, U.S. Appl. No, 11/364,153, filed Feb. 28, 2006, 62 pgs.
Office Action dated Apr. 29, 2009, U.S. Appl. No. 11/364,785, filed Feb. 28, 2006, 23 pgs.
Examiner's Search Strategy dated Apr. 29, 2009, U.S. Appl. No. 11/364,785, filed Feb. 28, 2006, 19 pgs.
Office Action dated Apr. 9, 2009, U.S. Appl. No. 12/170,884, filed Jul. 10, 2008, 10 pgs.
Response dated Oct. 9, 2009, U.S. Appl. No. 12/170,884, filed Jul. 10, 2008, 3 pgs.
Examiner's Search Strategy dated Feb. 19, 2010, U.S. Appl. No. 12/170,884, filed Jul. 10, 2008, 26 pgs.
Examiner's Interview Summary dated Feb. 19, 2010, U.S. Appl. No. 12/170,884, filed Jul. 10, 2008, 4 pgs.
Notice of Allowance dated 2/19/10, U.S. Appl. No. 12/170,884, filed Jul. 10, 2008, 5 pgs.
Office Action dated Mar. 5, 2009, U.S. Appl. No. 11/740,959, filed Apr. 27, 2007, 30 pgs.
Response dated Sep. 3, 2009, U.S. Appl. No. 11/740,959, filed Apr. 27, 2007, 12 pgs.
Examiner's Search Strategy dated Mar. 5, 2009, U.S. Appl. No. 11/740,959, filed Apr. 27, 2007, 12 pgs.
Final Office Action dated Jan. 20, 2010; U.S. Appl. No. 11/740,959, filed Apr. 27, 2007, 33 pgs.
Examiner's Search Strategy dated Jan. 20, 2010, U.S. Appl. No. 11/740,959, filed Apr. 27, 2007, 6 pgs.
Office Action dated Apr. 13, 2009, U.S. Appl. No. 11/097,939, filed Apr. 4, 2005, 12 pgs.
Amendment and Response dated Sep. 14, 2009, U.S. Appl. No. 11/097,939, filed Apr. 4, 2005, 8 pgs.
Examiner's Search Strategy dated Apr. 13, 2009, U.S. Appl. No. 11/097,939, filed Apr. 4, 2005, 3 pgs.
Final Office Action dated Feb. 17, 2010, U.S. Appl. No. 11/097,939, filed Apr. 4, 2005, 16 pgs.
Examiner's Search Strategy dated Feb. 17, 2010, U.S. Appl. No. 11/097,939, filed Apr. 4, 2005, 2 pgs.
Office Action dated Mar. 19, 2009, U.S. Appl. No. 11/554,855, filed Oct. 31, 2006, 11 pgs.
Response dated Aug. 19, 2009, U.S. Appl. No, 11/554,855, filed Oct. 31, 2006, 7 pgs.
Examiner's Search Strategy dated Mar. 19, 2009, U.S. Appl. No. 11/554,855, filed Oct. 31, 2006, 3 pgs.
Office Action dated Dec. 4, 2009, U.S. Appl. No. 11/554,855, filed Oct. 31, 2006, 15 pgs.
Examiner's Search Strategy dated Dec. 4, 2009, U.S. Appl. No. 11/554,855, filed Oct. 31, 2006, 3 pgs.
Office Action dated Mar. 19, 2009, U.S. Appl. No. 11/745,515, filed May 8, 2007, 11 pgs.

Office Action dated Dec. 4, 2009, U.S. Appl. No. 11/745,515, filed May 8, 2007, 16 pgs.
Examiner's Search Strategy dated Mar. 19, 2009, U.S. Appl. No. 11/745,515, filed May 8, 2007, 3 pgs.
Response dated Aug. 19, 2009, U.S. Appl. No. 11/745,515, filed May 8, 2007, 8 pgs.
Examiner's Search Strategy dated Dec. 4, 2009, U.S. Appl. No. 11/745,515, filed May 8, 2007, 3 pgs.
Office Action dated Oct. 11, 2005, U.S. Appl. No. 10/882,613, filed Jul. 1, 2004, 7 pgs.
Examiner's Search Strategy dated Oct. 2, 2005, U.S. Appl. No. 10/882,613, filed Jul. 1, 2004, 17 pgs.
Advisory Action dated Mar. 16, 2007, U.S. Appl. No. 10/444,892, filed May 22, 2003, 2 pgs.
Advisory Action dated Mar. 29, 2007, U.S. Appl. No. 10/444,892, filed May 22, 2003, 3 pgs.
Examiner's Interview Summ. Dated Oct. 4, 2007, U.S. Appl. No. 10/444,892, filed May 22, 2003, 2 pgs.
Final Office Action dated Aug. 29, 2006, U.S. Appl. No. 10/444,892, filed May 22, 2003, 7 pgs.
Office Action dated Mar. 1, 2006, U.S. Appl. No. 10/444,892, filed May 22, 2003, 5 pgs.
Amendment After Final dated Feb. 28, 2007, U.S. Appl. No. 10/444,892, filed May 22, 2003, 8 pgs.
Amendment dated Jun. 27, 2006, U.S. Appl. No. 10/444,892, filed May 22, 2003, 5 pgs.
Office Action dated Jul. 2, 2007, U.S. Appl. No. 11/110,449, filed Apr. 20, 2005, 11 pgs.
Examiner's Search Strategy dated Jun. 20, 2007, U.S. Appl. No. 11/110,449, filed Apr. 20, 2005, 7 pgs.
Office Action dated Jun. 29, 2009, U.S. Appl. No. 11/960,957, filed Oct. 20, 2007, 12 pgs.
Response dated Dec. 29, 2009, U.S. Appl. No. 11/960,957, filed Oct. 20, 2007, 10 pgs.
Examiner's Search Strategy dated Jun. 29, 2009, U.S. Appl. No. 11/960,957, filed Oct. 20, 2007, 1 pgs.
Notice of Non-Compliant Amendment dated Mar. 10, 2010, U.S. Appl. No. 11/960,957, filed Oct. 20, 2007, 2 pgs.
Amendment and Response to Notice of Non-Compliant Amendment dated Apr. 9, 2010, U.S. Appl. No. 11/960,957, filed Oct. 20, 2007, 5 pgs.
Office Action dated Jan. 26, 2007, U.S. Appl. No. 11/178,716, filed Jul. 11, 2005, 8 pgs.
Office Action dated Apr. 14, 2006, U.S. Appl. No. 11/178,716, filed Jul. 11, 2005, 8 pgs.
Amendment dated Jul. 25, 2006, U.S. Appl. No. 11/178,716, filed Jul. 11, 2005, 5 pgs.
Examiner's Search Strategy dated Jan. 21, 2007, U.S. Appl. No. 11/178,716, filed Jul. 11, 2005, 1 pg.
Examiner's Search Strategy dated Mar. 30, 2006, U.S. Appl. No. 11/178,716, filed Jul. 11, 2005, 15 pgs.
Examiner's Search Strategy dated Apr. 11, 2006, U.S. Appl. No. 11/178,716, filed Jul. 11, 2005, 1 pg.
Final Office Action dated May 18, 2007, U.S. Appl. No. 11/218,107, filed Sep. 1, 2005, 11 pgs.
Office Action dated Aug. 15, 2006, U.S. Appl. No. 11/218,107, filed Sep. 1, 2005, 8 pgs.
Response dated Feb. 14, 2007, U.S. Appl. No. 11/218,107, filed Sep. 1, 2005, 4 pgs.
Examiner's Search Strategy dated Jun. 30, 2006, U.S. Appl. No. 11/218,107, filed Sep. 1, 2005, 8 pgs.
Examiner's Search Strategy dated Aug. 11, 2006, U.S. Appl. No. 11/218,107, filed Sep. 1, 2005, 2 pgs.
Office Action dated Aug. 26, 2008, U.S. Appl. No. 11/940,655, filed Nov. 15, 2007, 7 pgs.
Office Action dated Sep. 28, 2009, U.S. Appl. No. 11/997,567, filed Mar. 21, 2008, 7 pgs.
Examiner's Search Strategy dated Sep. 28, 2009, U.S. Appl. No. 11/997,567, filed Mar. 21, 2008, 43 pgs.
Response dated Feb. 19, 2010, U.S. Appl. No. 11/997,567, filed Mar. 21, 2008, 10 pgs.
Examiner's Interview Summ. dated Oct. 2, 2009, U.S. Appl. No. 11/837,959, filed Aug. 13, 2007, 2 pgs.
Office Action dated Jul. 20, 2009, U.S. Appl. No. 11/837,959, filed Aug. 13, 2007, 8 pgs.
Examiner's Search Strategy dated Jul. 20, 2009, U.S. Appl. No. 11/837,959, filed Aug. 13, 2007, 5 pgs.
Final Office Action dated Mar. 25, 2010, U.S. Appl. No. 11/837,959, filed Aug. 13, 2007, 12 pgs.
Response dated Jan. 20, 2010, U.S. Appl. No. 11/837,959, filed Aug. 13, 2007, 11 pgs.
Ferger et al., Flibanserin, a drug intended for treatment of hypoactive sexual desire disorder in pre-menopausal women, affects spontaneous motor activity and brain neurochemistry in female rates, Naunyn Schmiedebergs Arch Pharmacol., Apr. 27, 2010, pp. 1-17 (epub ahead of print).
Aubert et al., Comparison of Flibanserin With the 5-Ht1a Agonist (+)-8-Oh-Dpat in Affecting Interactions Between Male-Female Marmoset Pairs, J. Sex Med., May 2010, 7(s3):118. (abstract).
Aubert et al., Initial PET Assessment of Flibanserin-induced Neural Changes in Female Marmoset Monkeys, J. Sex Med., May 2010, 7(s3):131. (abstract).
Aubert et al., Chronic Treatment of Female Marmoset Monkeys with (+)-8-OH-DPAT or Flibanserin Differentially Alters Response of the Hypothalamic-Pituitary-Adrenal Axis to Restraint and Acute Serotonergic Challenge, J. Sex Med., May 2010, 7(s3):131. (abstract).
Gelez et al., Chronic Flibanserin Treatment Increases Solicitations in the Female Rat, J. Sex Med., May 2010, 7(s3):118. (abstract).
Allers et al., Acute and Repeated Flibanserin Administration in Female Rats Modulates Monoamines Differentially Across Brain Areas: a Microdialysis Study, J. Sex Med., Feb 2010, 33 pgs. (Epub ahead of print).
Goldfischer et al., Efficacy of Continued Flibanserin Treatment on Sexual Desire, Satisfying Sexual Events and Sexual Functioning in Premenopausal Women With HSDD: Results From the Researching Outcomes on Sustained Efficacy (ROSE) Study, International Society for the Study of Womens Sexual Health (ISSWSH) annual meeting, 2008, 17 pgs. (oral presentation).
Final Office Action dated May 21, 2010, U.S. Appl. No. 11/997,567, filed Mar. 21, 2008, 7 pgs.
Final Office Action dated May 27, 2010, U.S. Appl. No. 11/278,551, filed Apr. 4, 2006, 8 pgs.
Examiner's Search Strategy dated May 27, 2010, U.S. Appl. No. 11/278,551, filed Apr. 4, 2006, 3 pgs.
Response dated Jun. 4, 2010, U.S. Appl. No. 11/554,855, filed Oct. 31, 2006, 10 pgs.
Response dated Jun. 4, 2010, U.S. Appl. No. 11/745,515, filed May 8, 2007, 8 pgs.
Restriction Requirement dated May 24, 2004 U.S. Appl. No. 10/210,474, filed Aug. 1, 2002 now US Pat. No. 7183410, issued Feb. 27, 2007, 6 pgs.
Response to Restriction Requirement dated Jun. 9, 2004 U.S. Appl. No. 10/210,474, filed Aug. 1, 2002 now US Pat. No. 7183410, issued Feb. 27, 2007, 2 pgs.
Restriction Requirement dated Aug. 20, 2008, U.S. Appl. No. 11/097,939, filed Apr. 4, 2005, 8 pgs.
Response to Restriction Requirement dated Feb. 12, 2009, U.S. Appl. No. 11/097,939, filed Apr. 4, 2005, 2 pgs.
Restriction Requirement dated Feb. 8, 2007, U.S. Appl. No. 11/110,449, filed Apr. 20, 2005, 8 pgs.
Response to Restriction Requirement dated Jun. 7, 2007, U.S. Appl. No. 11/110,449, filed Apr. 20, 2005, 2 pgs.
Restriction Requirement dated Dec. 23, 2008, U.S. Appl. No. 11/187,422, filed Jul. 22, 2005, 11 pgs.
Restriction Requirement dated May 23, 2007, U.S. Appl. No. 11/364,153, filed Feb. 28, 2006, 7 pgs.
Response to Restriction Requirement dated Sep. 24, 2007, U.S. Appl. No. 11/364,153, filed Feb. 28, 2006, 2 pgs.
Restriction Requirement dated Dec. 18, 2006, U.S. Appl. No. 11/381,590, filed Apr. 4, 2006, 7 pgs.
Response to Restriction Requirement dated Mar. 9, 2007, U.S. Appl. No. 11/381,590, filed Apr. 4, 2006, 2 pgs.
Restriction Requirment dated Aug. 18, 2008; U.S. Appl. No. 11/740,959, filed Apr. 27, 2007, 9 pgs.

Response to Restriction Requirment dated Nov. 18, 2008; U.S. Appl. No. 11/740,959, filed Apr. 27, 2007, 6 pgs.
Restriction Requirement dated Jun. 21, 2010, U.S. Appl. No. 11/956,949, filed Dec. 14, 2007, 7 pgs.
Restriction Requirement dated Feb. 5, 2009, U.S. Appl. No. 11/960,957 filed Oct. 20, 2007, 8 pgs.
Response to Restriction Requirement dated Mar. 4, 2009, U.S. Appl. No. 11/960,957, filed Oct. 20, 2007, 2 pgs.
Restriction Requirement dated Jun. 30, 2009, U.S. Appl. No. 11/997,567, filed Mar. 21, 2008, 7 pgs.
Response to Restriction Requirement dated Jul. 23, 2009, U.S. Appl. No. 11/997,567, filed Mar. 21, 2008, 2 pgs.
Restriction Requirement dated May 4, 2010, U.S. Appl. No. 12/279,589, filed Sep. 26, 2008 , 9 pgs.
RCE dated May 19, 2010, U.S. Appl. No. 12/170,884, filed Jul. 10, 2008, 3 pgs.
Examiner's Interview dated Apr. 15, 2009, U.S. Appl. No. 11/524,268 filed Sep. 21, 2006, 4pgs.
Examiner's Interview dated Oct. 23, 2007, U.S. Appl. No. 11/524,268, filed Sep. 21, 2006, 1 pg.
Notice of Allowance dated Jan. 11, 2010, U.S. Appl. No. 11/524,268, filed Sep. 21, 2006, 7 pgs.
Office Action dated Feb. 11, 2008, U.S. Appl. No. 11/524,268, filed Sep. 21, 2006, 15 pgs.
Office Action dated May 2, 2007, U.S. Appl. No. 11/524,268, filed Sep. 21, 2006, 10 pgs.
Office Action dated Dec. 1, 2008, U.S. Appl. No. 11/524,268, filed Sep. 21, 2006, 16 pgs.
Amendment dated Jun. 1, 2009, U.S. Appl. No. 11/524,268 filed Sep. 21, 2006, 64 pgs.
Response dated Aug. 11, 2008, U.S. Appl. No. 11/524,268, filed Sep. 21, 2006, 15 pgs.
Response dated Nov. 2, 2007, U.S. Appl. No. 11/524,268, filed Sep. 21, 2006, 32 pgs.
Examiner's Search Strategy dated Jan. 11, 2010, U.S. Appl. No. 11/524,268, filed Sep. 21, 2006, 5 pgs.
Examiner's Search Strategy dated Dec. 1, 2008, U.S. Appl. No. 11/524,268, filed Sep. 21, 2006, 4 pgs.
RCE dated Apr. 9, 2010, U.S. Appl. No. 11/524,268, filed Sep. 21, 2006, 2 pgs.
Office Action dated Jan. 11, 2010, U.S. Appl. No. 11/837,962, filed Aug. 13, 2007, 17 pgs.
Examiner's Search Strategy dated Jan. 11, 2010, U.S. Appl. No. 11/837,962, filed Aug. 13, 2007, 8 pgs.
Response dated Jun. 11, 2010 U.S. Appl. No. 11/837,962, filed Aug. 13, 2007, 16 pgs.
Restriction Requirement dated Sep. 9, 2009, U.S. Appl. No. 11/837,962, filed Aug. 13, 2007, 10 pgs.
Response to Restriction Requirement dated Sep. 25, 2009, U.S. Appl. No. 11/837,962, filed Aug. 13, 2007, 2 pgs.
Office Action dated Jan. 14, 2010, U.S. Appl. No. 12/091,848, filed Apr. 28, 2008, 5 pgs.
Examiner's Search Strategy dated Jan. 14, 2010, U.S. Appl. No. 12/091,848, filed Apr. 28, 2008, 47 pgs.
Response dated Jun. 14, 2010 U.S. Appl. No. 12/091,848, filed Apr. 28, 2008, 5 pgs.
Restriction Requirement dated Oct. 7, 2009, U.S. Appl. No. 12/091,848, filed Apr. 28, 2008, 5 pgs.
Response to Restriction Requirement dated Nov. 9, 2009, U.S. Appl. No. 12/091,848, filed Apr. 28, 2008, 9 pgs.
Notice of Non-Compliant Amendment dated Jun. 22, 2010 U.S. Appl. No. 12/091,848, filed Apr. 28, 2008, 2 pgs.
Response to Notice of Non-Compliant Amdmt dated Jun. 23, 2010 U.S. Appl. No. 12/091,848, filed Apr. 28, 2008, 6 pgs.
Final Office Action dated Jul. 9, 2010; U.S. Appl. No. 11/960,957, filed Dec. 20, 2007, 9 pgs.
U.S. Appl. No. 08/039,002, filed Mar. 25, 1993, Bietti.
U.S. Appl. No. 11/956,949, filed Dec. 14, 2007, Lewis-D'Agostino et al.
U.S. Appl. No. 12/390,665, filed Feb. 23, 2009, Wunderlich et al.
U.S. Appl. No. 12/532,269, filed Dec. 14, 2009, Boeck et al.
U.S. Appl. No. 12/675,231, filed Feb. 25, 2010, Hanes et al.

Anonymous, Hormone Patch may Provide Some Increase in Sexual Desire in Menopausal Women, Jul. 25, 2005, URL:http://pubs.ama-assn.org/media/2005a/0725.dtl, 2 pgs.
Bechard, et al., Int. J. Pharm., 1992, 87:133-139.
Braiman, Psychosexual disorders of young adulthood, Clin Obstetrics and Gynecology, 1970, 13(3):734-745.
Byrn, et al., Hydrates and Solvates, Solid State Chemistry & Drugs, 1999, Chpt. 11, pp. 233-247.
Buhrich, et al., Can fetishism occur in transexuals?, Arch Sex Behav, 1977, 6(3):223-235.
Butts, The relationship between sexual addiction and sexual dysfunction, J. Health Care Underserved, 1992, 3(1):128-35; discussion 136-7.
Buvat, et al., Role of hormones in sexual dysfunction, homosexuality, transsexualism, and paraphilia related disorders. Diagnostic and therapeutic consequences, Contracept Fertil Sex, 1996, 24(11):834-846-only English abstract.
Bymaster, et al., Fluoxetine, but not other selective serotonin uptake inhibitors, increases norepinephrine and dopamine extracellular levels in prefrontal cortex, Psychopharmacology, 2002, 160:353-361.
Chiao, et al., Remington Pharm 19$^{th}$ Ed., Panamerican Spain, 1988, pp. 2535-2537.
Cooper, et al., A female sex offender with multiple paraphilias: a psychologic, physiol ogic (laboratory sexual arousal) and endocrine case study, Can J Psychiatry, 1990, 35(4):334-7.
Grau, et al., Risk Factors, Outcome, and Treatment in Subtypes of Ischemic Stroke: The German Stroke Data Bank, Stroke, 2001; 32:2559-2566.
Guarrati, et al: Coffee, Tea and Me: Moderate doses of caffeine affect sexual behavior in female rats, Pharma Biochem and Behavior, Nov. 2005, 82(3):522-530. ISSN: 0091-3057 Elsevier, US, abstract.
Kafka, A Monoamine Hypothesis for the Pathophysiology of Paraphilic Disorders, Archives of Sex Behav, 1997, 26(4):343-58.
Marshall, et al., Unified Approach to the Analysis of Genetic Variation in Serotonergic Pathways, Am J. Med. Genetics Neurophychiatric Genetics, 1999, 88:621-627.
Moser, Lust, lack of desire and paraphilias: some thoughts and possible connections, Marital Ther, 1992, 18(1):65-9.
Mutschler et al., The Effect of Drugs: Antidepressive Agents, Manual of Pharmacology and Toxicology, 2001, 8th Ed, pp. 171-172, Scientific Publishing Company PLC, Stuttgart.
Otsuka, et al., Chem. Pharm. Bull., 1999, 47(6):852.856.
Pharmacopia, 1995, p. 1843.
Schwartz, et al., Conceptual factors in the treatment of paraphilias: a preliminary rep., Maritial Ther, 1983, 9(2):3-18.
Semkova, et al., Neuroprotective effect of 5-HT1A receptor agonist, Bay x 3702, demonstrated in vitro and in vivo, Euro J Pharm, 1998, 359:251-260.
Singhal, et al., Advanced Drug Delivery Reviews, 2004, 56:335-347.
Soederberg, et al., Leptin is a Risk Marker for First-Ever Hemorrhagic Stroke in a Population-Based Cohort, Stroke, J1 of the Am Heart Assoc., 1999; 30:328-337.
Stedman'S Medical Dictionary definition "Anxiety", 28$^{th}$ Ed., 2006, p. 114, Lippincott Williams & Wilkins, Baltimore MD.
Thrombolytic Therapy: MedlinePlus Medical Encyclopedia, http://www.nlm.nih.gov/medlineplus/ency/article/007089.htm, accessed Dec. 17, 2009, pp. 1-4.
Vippagunta, Acv. Drug Del. Rev., 2001, 48:3-26.
Welsh, et al., Effect of Lactacidosis on Pyridine Nucleotide Stability During Ischemia in Mouse Brain, J Neurochemistry, 1987, 49(3):846-851.
Zverina, et al., The occurrence of atypical sexual experience among various female groups, Arch Sex Behav, 1987, 16(4):321-6.
Aizenberg et al, "Cyproheptadine Treatment of Sexual Dysfunction Induced by Serotonin Reuptake Inhibitors," Clinical Neuropharmacology, vol. 18, No. 4, pp. 320-324, 1995 Lippincott-Raven Publishers, Philadelphia.
Archer, T.; "5-HT, Pain and Anxiety" Behavioural Pharmacology of 5-HT, pp. 299-300 (1989).
Chemical Abstract 88-98788c (Apr. 10, 1978),Awouters et al, "Oxatomide, a new orally active drug which inhibits both the release and the effects of allergic mediators,".

Backhauss et al., "A Mouse Model of Focal Cerebral Ischemia for Screening Neuroprotective Drug Effects," Journal of Pharmacological Methods 27, 1992, pp. 27-32.

Basson, R. et al; "Report of the international consensus development conference on female sexual dysfunction: definitions and classifications;" The Journal of Urology; vol. 163 pp. 888-893, Mar. 2000.

Baxter,G., "5-$HT_2$ Receptor Subtypes: a family re-united?", Trends in Pharmacological Sciences, Elsevier, Haywarth, GB, vol. 16, No. 3, Mar. 1995, pp. 105-110.

Beers, M.H. et al; The Merck Manual of Diagnosis and Therapy; 17th Ed., 1999, pp. 1595-1598.

Bernstein, J. et al; "Concomitant Polymorphs"; Angewandte Chemie, Int. Ed., 1999, pp. 3441-3461.

Bevan et al; "5-HT and sexual behaviour" Behavioural Pharmacology of 5-HT, pp. 33-34, 87-88 (1989).

Borsini, F. et al; Behavioral Effects of Flibanserin (BIMT 17), Sep. 1999, Pharmacology, Biochemistry and Behavior, vol. 64, Issue 1, abstract.

Borsini, F. et al; Behavioral Effects of Flibanserin (BIMT 17), Sep. 1999, Pharmacology Biochemistry and Behavior, vol. 64, Issue 1, pp. 137-146.

Borsini, F. et al; "Flibanserin," Drugs of the future, (1998) vol. 23 (1) pp. 9-16.

Borsini, F. et al; "BIMT 17, a 5-$HT_{2A}$ receptor antagonist and 5-$HT_{1A}$ receptor full agonist in rat cerebral cortex"; Naunyn-Schmiedeberg's Archives of Pharm., 1995, 352 pp. 276-282.

Borsini, F. et al; "Lack of interaction between flibanserin and antidepressants in inducing serotonergic syndrome in rats" International Journal of Neuropsychopharmacology (2001) pp. 9-15, vol. 4, No. 1, University Press, Cambridge, GB.

Borsini, F. et al, "Mechanism of action of flibanserin in the learned helplessness paradigm in rats," European Journal of Pharmacology 433:81-89 (2001).

Borsini, F. et al; "Pharmacology of Flibanserin" CNS Drug Reviews 2002; vol. 8, No. 2, pp. 117-142.

Borsini, F. et al., "BIMT 17: a putative antidepressant with a fast onset of action?" Psychopharmacology (1997) 134:378-386.

Brambilla et al., "Effect of Flibanserin (BIMT 17), fluoxetine 8-OH-DPAT and busprione on serotonin synthesis in rat brain," Europ. Neuropsychopharmacology, Vo. 10, No. 1, 1999, pp. 63-67.

Carey, John, "Viagra for Women?" Business Week.com (Dec. 28, 2006).

R. Cesana et al; "The effect of MIMT 17, a new potential antidepressant, in the forced swimming test in mice" Behavioral Pharmacology (1995) pp. 688-694, vol. 6. Rapid Science Publishers, GB.

Chalmers et al; "Corticotrophin-releasing factor receptors: from molecular biology to drug design" TiPS vol. 17 pp. 166-172, Apr. 1996.

Chemical Abstracts Service, Columbus 1978, Damir et al., "Hemodynamic effects of pharmacological block during acute overload of the heart" Database accession # 1978:591197 XP-002436715.

Chemical Abstract: Database, Collino, F. et al; accession No. 98:16650: "Mannich bases of bensimidazoles, benzotriazoles and other analogous compounds, with pharmacological activity."-XP002197885 dated 1983 (see "AN").

Cloninger, C.R.; "A systematic method for clinical description and classification of personality variants" Arch. Gen. Psychiatry, vol. 44 pp. 573-588 (Jun. 1987).

Cools, A.R.; "Depression and psychosis" Behavioural Pharmacology of 5-HT, pp. 153-155 (1989).

Cremers and Boehm, "Non Erectile Dysfunction Application of Sildenafil", Herz, vol. 28, No. 4, pp. 325-333, 2003.

Crook, T. and Larkin, M.; "Effects of ondansertron in age-associated memory impairment" The role of ondansetron, a novel 5-HT3 antagonist, in the treatment of psychiatric disorders, 5th World Congress of Biochemical Psychiatry, pp. 21-23 (1991).

Cyr, Monica et al; "Nefazodone: Its place among antidepressants," Annals of Pharmacotherapy, vol. 30 No. 9 pp. 1006-1012; 1996.

Chemical Abstract 118-124537e Damour et al, "Preparation and formulation of 1[(4-phenylpiperazino)alkyl]benzimidazolin-2-ones and analogs as serotonin $S_2$ antagonists"( Mar. 29, 1993).

Darlington, C.; "Flibanserin Boehringer Ingelheim Corp."; Current Opinion in CPNS investigational drugs vol. 1, No. 4, 1999, pp. 510-513; Pharma Press Ltd, London, GB.

DeVry, J.;"5-$HT_{1A}$ receptors in psychopathology and the mechanism of action of clinically effective therapeutic agents" Drug News and Perspectives 1996, vol. 9 No. 5 pp. 270-280.

Deangelis, L.; "5-$HT_{2A}$ antagonists in psychiatric disorders;" Current Opinion in Investigational Drugs 2002; vol. 3 No. 1 pp. 106-112; ISSN: 1472-4472.

Dimmock, P. et al; "Efficacy of selective serotonin-reuptake inhibitors in premenstrual syndrome: A systematic review" The Lancet, vol. 356, No. 9236 pp. 1131-1136, Sep. 30, 2000.

Fourcroy, Jean L. ; "Female sexual dysfunction: potential for pharmaotherapy" Drugs 2003, vol. 63 No. 14 pp. 1445-1457.

Frampton, et al; "Pentoxifylline ( Oxpentifylline) a Review of its Therapeutic Efficacy in the Management of Peripheral Vascular and Cerebrovascular Disorders;" (Drug Evaluation) Drugs and Aging 7 (6) pp. 480-503, 1995.

Fujikura et al; "Effects of naftidrofuryl oxalate, a 5-HT2 antagonist, on neuronal damage and local cerebral blood flow following transient cerebral ischemia in gerbils;" Brain Research 636 (1994) pp. 103-106.

Geyer, M.; "5-$HT_2$ antagonists increase tactile startle habituation in an animal model of habituation deficit in schizophrenia" Behavioural Pharmacology of 5-HT, pp. 243-246 (1989).

Giron, D; "Thermal analysis and calorimetric methods in the characterisation of polymorphs and solvates"; Thermochimica ACTA, Elsevier Science; 248; 1995; pp. 1-59.

Goa, et al; "Buspirone. A preliminary review of its pharmacological properties and therapeutic efficacy as an anxiolytic;" Drugs 1986 vol. 32 pp. 114-129.

Gonzales, "Natural Compound May Offer New Treatment for Chronic Pain" NIDA Notes, vol. 16, No. 3-Aug. 2001, www.nida.nih.gov/NIDA_Notes/NNVol16N3/Natural.htm.

Gould;" Salt selection for basic drugs;" International Journal of Pharmaceutics; vol. 33, Issue 1-3, pp. 201-217, Nov. 1986.

Greene, T.; "Protective groups in organic synthesis:", Harvard University pp. 10-17 (1981), Wiley-Interscience Publication).

Hansenne, M. et al; "Harm avoidance dimension of the tridimensional personality questionnaire and serotonin-1A activity in depressed patients;" Biol. Psychiatry 1997, vol. 42 pp. 959-961.

Invernizzi et al,"Flibanserin, a potential antidepressant drug, lowers 5-HT and raises dopamine and noradrenaline in the rat prefrontal cortex dialysate: role of 5-$HT_{1A}$ receptors"; British Journal of Pharmacology, vol. 139 pp. 1281-1288, Jun. 2003.

Kleven, M., "Modification of behavioral effects of 8-hydroxy-2-(di-n-propylamino) tetralin following chronic ethanol consumption in the rat: evidence for the involvement of 5-$HT_{1A}$ receptors in ethanol dependence.", European Journal of Pharmacology, 1995, vol. 281, No. 3, pp. 219-228.

Caplus abstract 1999:285050, KOBA, "Involvement of peripheral 5-$HT_{2A}$ receptor activation in pain behavior evoked by formalin paw injection in the rat," Kyushu Shika Gakkai Zaahi 53(1):253-60 (1999).

Lammers, GJ. et al; "Ritanserin, a 5-$HT_2$ receptor blocker, as add on treatment in narcolepsy;" Sleep 1991, vol. 14, No. 2 pp. 130-132.

Leonard, B.E.; "Sub-types of serotonin receptors: biochemical changes and pharmacological consequences" International Clinical Psychopharmacology 7, pp. 13-21 (1992).

Lyrer, "Neue Ansatze in der Akutbehandlung des zerebrovaskularen Insultes(New Approaches in the Acute Treatment of Cerebrovascular Insult)" Schweiz. Med. Wochenschr. vol. 124 No. 45 pp. 2005-2012 (1994).

Marazziti, Donatella et al; "Region-dependent effects of flibanserin and buspirone on adenylyl cyclase activity in the human brain" Int'l Journal of Neuropsychopharmacology, Jun. 2002, p. 131-140, vol. 5, No. 2.

Martindale: "Anxiolytic Sedatives Hypnotics and Antipsychotics" The complete drug reference, 1999, p. 635, Pharmaceutial Press, London 32.

McCall, RB. et al; "Role of serotonin 1A and serotonin 2 receptors in the central regulation of the cardiovascular system;" Pharmacological Reviews 1994, vol. 46 No. 3 pp. 231-243.

Merriam Webster New Collegiate Dictionary, definition of Diagnosis, 1981, p. 311.
Meston and Gorzalka, "Psychoactive Drugs and Human Sexual Behavior: The Role of Serotonergic Activity," Journal of Psychoactive Drugs, vol. 24(1), Jan.-Mar. 1992 pp. 1-40.
"The Merck Manual of diagnosis and therapy", Merck Research Laboratories, USA 1999, p. 1410, col. 1-p. 1413, col. 2, paragraph 1; p. 1412, tables 173-2 XP-002439435.
Miranda, et al., Dexketoprofen-Induced antinociception in animal models of acute pain: Synergy with morphine and paracetamol; Neuropharmacology 52 (2007) 291-296.
Moynihan, R., "The making of disease: female sexual dysfunction" British Medical Journal, 2003. vol. 326, pp. 45-47.
Nadeson, et al., "Antinociceptive role of 5-HT$_{1A}$ receptors in rat spinal cord" Laboratory Investigations, British Journal of Anaesthesia 88(5):679-84 (2002).
Okamoto et al., "5-HT2A receptor subtype in the peripheral branch of sensory fibers is involved in the potentiation of inflammatory pain in rats," Pain 99 (2002) 133-143.
Petkov, V.D. et al; " Participation of different 5-HT receptors in the memory process in rats and its modulation by the serotonin depletory p-chlorophenylalanine;" Acta Neurobiol. Exp. 1995 vol. 55 pp. 243-252.
Philips & Slaughter; "Depression and Sexual Desire," American Family Physician, vol. 62/No. 4, Aug. 15, 2000.
Podhorna, J. et al; "Flibanserin has anxiolytic effects without locomotor side effects in the infant rat ultrasonic vocalization model of anxiety;" British Journal of Pharacology (2000) vol. 130 No. 4 pp. 739-746.
Prehn et al; "Neuroprotective properties of 5-HT1A receptor agonists in rodent models of focal and global cerebral ischemia;" European Journal of Pharmacology, 203 (1991) 213-222.
Prehn et al., "Effects of serotonergic drugs in experimental brain ischemia: evidence for a protective role of serotonin in cerebral ischemia;" Brain Research 630 (1993) pp. 10-20.
Riekkinen et al; "The effects of increased serotonergic and decreased cholinergic activities on spatial navigation performance in rats" Pharmacology Biochemistry & Behavior, vol. 39 pp. 25-29 (1991).
Rueter, L.E. et al; "Electrophysiological examination of the effects of sustained flibanserin administration on serotonin receptors in rat brain;" British J. of Pharm, 1999, vol. 126, No. 3, pp. 627-638.
Risch, S. Craig et al; "Neurochemical alterations of serotonergic neuronal systems in depression;" J. Clin. Psychiatry 1992, vol. 53 No. 10 Suppl. 3-7.
Robinson, D.S. "Serotonin receptor subtypes and affective disorders;" Clinical Neuropharmacology 1993, vol. 16 No. Suppl. 3 pp. S1-S5.
Rosland et al., "The formalin test in mice: effect of formalin concentration," Pain 42 (1990) 235-242.
Shibata et al., "Ischemia-induced impairment of 2-deoxyglucose uptake and CA1 field potentials in rat hippocampal slices: protection by 5-HT1A receptor agonists and 5-HT2 receptor antagonists;" European Journal of Pharmacology, 229 (1992) pp. 21-29.
Shipton, B. et al., "Valvular heart disease: review and update," American Family PhysicianJun. 1, 2001, vol. 63 # 11, pp. 2201-2208.
Sietsema, D. et al, "From Taboo to Treatment?" Good Clinical Practice Journal, Jan. 2005, vol. 12, # 1, pp. 23-27.
Spine-health.com, Types of Back Pain: Acute Pain, Chronic Pain and Neuropathic Pain, www.spine-health.com/topics/cd/chronic_pain/chronicpain02.html, Oct. 2, 2007.
Steiner, M., Recognition of Premenstrual Dysphoric Disorder and Its Treatment; The Lancet, vol. 356, No. 9236, Sep. 30, 2000, pp. 1126-1127.
Vandenberk et al; Piperazine and piperidine derivatives, Chemical Abstract 88-50920n (Jan. 30, 1978).
Walsh K. et al., "Sexual dysfunction in the older women and overview of the current understanding and management" Drugs and Aging, 2004, vol. 21, # 10 pp. 655-675.
Zajecka, John et al; "Sexual function and satisfaction in the treatment of chronic major depression with nefazodone, psychotherapy, and their combination;" Journal Clin. Psychiatry, vol. 63 No. 8 pp. 709-716, Aug. 2002.

U.S. Appl. No. 11/956,949, filed Dec. 14, 2007, D. Lewis-D'Agostino et al.
U.S. Appl. No. 11/960,957, filed Dec. 20, 2007, Klaus Mendla et al.
U.S. Appl. No. 11/940,655, filed Nov. 15, 2007; Dolsten, Mikael.
U.S. Appl. No. 11/997,567, filed Feb. 1, 2008, Ceci, Angelo.
U.S. Appl. No. 11/837,962, filed Aug. 13, 2007, N. Pearnchob et al.
Berge et al., Pharmaceutical Salts, J Pharm Sci., 1977, 66(1):1-19.
Kumar et al., An Overview of Automated Systems Relevant in Pharmaceutical Salt Screening; Drug Discovery Today, 2007, 12(23-24):1046-1053.
Stahl et al., Handbook of Pharmaceutical Salts: Selection and Use, Helvetica Chim. Acta, 2002, pp. 1-7.
U.S. Appl. No. 13/131,926, filed May 31, 2011, Mazurek et al.
Eriksson, Serotonin reuptake inhibitors for the treatment of premenstrual dysphoria, Intl. Clin. Psychopharm, 1999, 14Supp2:S27-S33.
Steiner et al., Seretonin re-uptake inhibitors in the treatment of premenstrual dysphoria: Current status of knowledge, 1997, 1:241-247.
Response to Office Action dated Mar. 14, 2011; U.S. Appl. No. 11/097,939, filed Apr. 4, 2005, 20 pgs.
Interview Summary dated Mar. 15, 2011; U.S. Appl. No. 11/097,939, filed Apr. 4, 2005, 4 pgs.
Interview Summary dated Apr. 6, 2011; U.S. Appl. No. 11/997,567, filed Mar. 21, 2008, 3 pgs.
Response/Amendment dated Apr. 12, 2011; U.S. Appl. No. 11/997,567, filed Mar. 21, 2008, 9 pgs.
Final Office Action dated Apr. 19, 2011, U.S. Appl. No. 11/278,551, filed Apr. 4, 2006, 9 pgs.
Response to Office Action dated May 2, 2011; U.S. Appl. No. 12/390,665, filed Feb. 23, 2009, 11 pgs.
Office Action dated May 27, 2011, U.S. Appl. No. 12/170,884, filed Jul. 10, 2008, 6 pgs.
Office Action dated May 31, 2011; U.S. Appl. No. 11/097,939, filed Apr. 4, 2005, 15 pgs.
Final Office Action dated Jun. 16, 2011; U.S. Appl. No. 11/956,949, filed Dec. 14, 2007, 7 pgs.
Final Office Action dated Jun. 23, 2011; U.S. Appl. No. 11/997,567 filed Mar. 21, 2008, 7 pgs.
Restriction Requirement dated Jun. 29, 2011, U.S. Appl. No. 12/306,945, filed Feb. 9, 2009, 7 pgs.
U.S. Appl. No. 12/987,388, filed Jan. 10, 2011, Mendla et al.
Anderson et al., Guidelines for choice of selective serotonin reuptake inhibitor in depressive illness, Adv. Psychia. Treatment, 2001, 7:170-180.
Anonymous, Gel significantly increases sexual-activity in surgically menopausal women, Online, Nov. 1, 2004, XP002455243, Retrieved from the Internet: URL:http/www.news-medical.net/print_article.asp?id=5960>[retrieved on Oct. 17, 2007] 8 pgs.
Anonymous: "Hormone Patch May Provide Some Increase in Sexual Desire in Menopausal Women" Jul. 25, 2005; URL:http://pubs.ama-assn.org/media/2005a/0725.dtl , 2pgs.
Freeman et al., Differential Response to Antidepressants in Women With Premenstrual Syndrome/Premenstrual Dysphoric Disorder, Arch Gen Phych, 1999, 56:932-939.
Yekimov, Sex toys and devices in sexual dysfunction therapy, www.mosmedclinic.ru/conf_library/2002/2/130/, 2002, 6 pgs.
Richelson, Pharmacology of Antidepressants, Mayo Clin Proc., 2001, 76:511-527.
Werneke et al., Antidepressants and sexual dysfuntion, Acta Psychia. Scand, 2005, 114:384-397.
Response to Final Office Action dated Jul. 20, 2010; U.S. Appl. No. 11/740,959, filed Apr. 27, 2007, 14 pgs.
Restriction Requirement dated Oct. 4, 2005; U.S. Appl. No. 10/444,892, filed May 22, 2003, 7 pgs.
Response to Restriction Requirement dated Dec. 1, 2005; U.S. Appl. No. 10/444,892, filed May 22, 2003, 2 pgs.
RCE dated Jul. 20, 2010; U.S. Appl. No. 11/740,959, filed Apr. 27, 2007, 3pgs.
Response to Final Office Action dated Aug. 17, 2010; U.S. Appl. No. 11/097,939, filed Apr. 4, 2005, 22 pgs.
RCE dated Aug. 17, 2010; U.S. Appl. No. 11/097,939, filed Apr. 4, 2005, 3 pgs.
RCE dated Sep. 27, 2010, U.S. Appl. No. 11/837,959, filed Aug. 13, 2007, 2 pg.

Response to Final Office Action dated Sep. 27, 2010, U.S. Appl. No. 11/837,959, filed Aug. 13, 2007, 20 pgs.
Response to Final Office Action dated Sep. 27, 2010 U.S. Appl. No. 11/278,551, filed Apr. 4, 2006, 8 pgs.
Interview Summary dated Jul. 19, 2010; U.S. Appl. No. 11/740,959, filed Apr. 27, 2007, 3pgs.
Final Office Action dated Aug. 20, 2010 U.S. Appl. No. 11/745,515, filed May 8, 2007, 7 pgs.
Final Office Action dated Aug. 30, 2010 U.S. Appl. No. 11/554,855, filed Oct. 31, 2006, 10 pgs.
Notice of Missing Requirements dated Aug. 24, 2010 U.S. Appl. No. 12/675,231, filed Feb. 25, 2010, 2 pgs.
Interview Summary dated Aug. 25, 2010 U.S. Appl. No. 11/278,551, filed Apr. 4, 2006, 3 pgs.
Final Office Action dated Sep. 13, 2010, U.S. Appl. No. 11/837,962, filed Aug. 13, 2007, 20 pgs.
Office Action dated Sep. 14, 2010; U.S. Appl. No. 11/097,939, filed Apr. 4, 2005, 18 pgs.
Interview Summary dated Sep. 15, 2010, U.S. Appl. No. 11/837,959, filed Aug. 13, 2007, 4 pg.
Notice of Allowance dated Sep. 20, 2010 U.S. Appl. No. 12/091,848, filed Apr. 28, 2008, 7 pgs.
Response to Final Office Action dated Oct. 12, 2010; U.S. Appl. No. 11/960,957, filed Dec. 20, 2007, 16 pgs.
Interview Summary dated Oct. 19, 2010; U.S. Appl. No. 11/997,567, filed Mar. 21, 2008, 3 pgs.
Response to Final Office Action dated Oct. 21, 2010; U.S. Appl. No. 11/997,567, filed Mar. 21, 2008, 8 pgs.
RCE dated Oct. 21, 2010; U.S. Appl. No. 11/997,567, filed Mar. 21, 2008, 2 pgs.
Interview Substance dated Oct. 21, 2010; U.S. Appl. No. 11/997,567, filed Mar. 21, 2008, 1 pg.
Office Action dated Oct. 26, 2010, U.S. Appl. No. 11/278,551, filed Apr. 4, 2006, 10 pgs.
Office Action dated Nov. 5, 2010; U.S. Appl. No. 11/956,949, filed Dec. 14, 2007, 10 pgs.
Advisory Action dated Nov. 8, 2010; U.S. Appl. No. 11/960,957, filed Dec. 20, 2007, 3 pgs.
Acknowledgment of Priority Document dated Nov. 4, 2010; U.S. Appl. No. 12/091,848, filed Apr. 28, 2008, 1 pg.
Office Action dated Nov. 12, 2010; U.S. Appl. No. 11/997,567, filed Mar. 21, 2008, 7 pgs.
Notice of Allowance dated Nov. 15, 2010; U.S. Appl. No. 12/091,848, filed Apr. 28, 2008, 4 pgs.
RCE dated Dec. 20, 2010; U.S. Appl. No. 12/091,848, filed Apr. 28, 2008, 3 pgs.
Office Action dated Dec. 30, 2010; U.S. Appl. No. 12/390,665, filed Feb. 23, 2009, 9 pgs.
Response to Final Office Action dated Jan. 20, 2011; U.S. Appl. No. 11/745,515, filed May 8, 2007, 7 pgs.
Response to Final Office Action dated Jan. 20, 2011; U.S. Appl. No. 11/554,855, filed Oct. 31, 2006, 9 pgs.
Response to Office Action dated Jan. 28, 2011, U.S. Appl. No. 11/278,551, filed Apr. 4, 2006, 7 pgs.
RCE dated Feb. 15, 2011; U.S. Appl. No. 11/837,962, filed Aug. 13, 2007, 2 pgs.
Response to Final Office Action dated Feb. 15, 2011; U.S. Appl. No. 11/837,962, filed Aug. 13, 2007, 15 pgs.
Notice of Allowance dated Feb. 16, 2011; U.S. Appl. No. 12/091,848, filed Apr. 28, 2008, 8 pgs.
Notice of Appeal dated Feb. 22, 2011; U.S. Appl. No. 11/745,515, filed May 8, 2007, 1 pgs.
Notice of Appeal dated Feb. 22, 2011; U.S. Appl. No. 11/554,855, filed Oct. 31, 2006, 1 pgs.
Advisory Action dated Mar. 2, 2011; U.S. Appl. No. 11/745,515, filed May 8, 2007, 3 pgs.
Advisory Action dated Mar. 2, 2011; U.S. Appl. No. 11/554,855, filed Oct. 31, 2006, 3 pgs.
FDA (U.S. Food and Drug Administration); Reproductive Health Drugs Advisory Committee Meeting Announcement; URL: http://www.fda.gov/AdvisoryCommittees/Calendar/ucm210886.htm; Jun. 18, 2010; 1 pg.
Background Document for Meeting of Advisory Committee for Reproductive Health Drugs (Jun. 8, 2010); NDA 22-526 Flibanserin; Boehringer Ingelheim; May 20, 2010; 80 pgs.
Briefing Document; Flibanserin (BIMT 17 BS); Boehringer Ingelheim; May 14, 2010; 248 pgs.
FDA (U.S. Food and Drug Administration); Reproductive Health Drugs Advisory Committee Meeting; Draft Agenda; Jun. 18, 2010; 1 pg.
FDA (U.S. Food and Drug Administration); Reproductive Health Drugs Advisory Committee Meeting; Draft Questions to the Committee; Jun. 18, 2010; 1 pg.
FDA (U.S. Food and Drug Administration); Reproductive Health Drugs Advisory Committee Meeting; Draft Meeting Roster; Jun. 18, 2010; 2 pgs.
Advisory Committee for Reproductive Health Drugs—2010 Members; Jun. 2010; 2 pgs.
FDA (U.S. Food and Drug Administration); Reproductive Health Drugs Advisory Committee Meeting; Agenda; Jun. 18, 2010; 2 pgs.
FDA (U.S. Food and Drug Administration); Reproductive Health Drugs Advisory Committee Meeting; Questions to the Committee; Jun. 18, 2010; 1 pgs.
FDA (U.S. Food and Drug Administration); Reproductive Health Drugs Advisory Committee Meeting; Meeting Roster; Jun. 18, 2010; 2 pgs.
(Slides) Division of Reproductive and Urologic Drug Products Advisory Committee Meeting; Flibanserin (NDA-22526); Boehringer Ingelheim; Jun. 18, 2010; 110 pgs.
Press Release May 19, 2010; women with hypoactive sexual desire disorder (HSDD) report that fibanserin increased their sexual desire and reduced associated distress; http://www.boehringer-ingelheim.com/news/news releases/press releases/2010/May 19, 2010;; 4 pgs.
Press Release Jun. 17, 2010; Key Facts on HSDD and Flibanserin; http://us.boerhinger-ingelheim.com/news events/press releases/press release archive/2010; 2 pgs.
Press Release Jun. 18, 2010; Boehringer Ingelheim comments on Jun. 18th FDA Advisory Committee Meeting; http://us.boehringer-ingelheim.com/news events/press releases; press release archive/2010; 2 pgs.
FDA (U.S. Food and Drug Administration); Transcript of Advisory Committee for Reproductive Health Drugs; Jun. 18, 2010; 293 pgs.

* cited by examiner

EXTENDED RELEASE TABLET FORMULATIONS OF FLIBANSERIN AND METHOD FOR MANUFACTURING THE SAME

This application claims the benefit of priority to EP 06 118 896, filed Aug. 14, 2006, the contents of which are incorporated herein by reference in its entirety.

FIELD OF THE INVENTION

The present invention is directed to an extended release system, particularly for oral administration, of flibanserin and a method for the production thereof.

BACKGROUND OF THE INVENTION

The invention relates to novel extended release systems for basic drugs with pH-dependent water solubility such as flibanserin. Flibanserin is a known benzimidazolon derivative having the summation formula $C_{20}H_{21}F_3N_4O$ represented by the chemical indication 1,3-dihydro-1-[2-[4-[3-(trifluoromethyl)phenyl]-1-piperazinyl]ethyl]-2H-benzimidazole-2-one which was already disclosed in 1992 in form of its hydrochloride in EP-A-526 434 and has the following chemical formula:

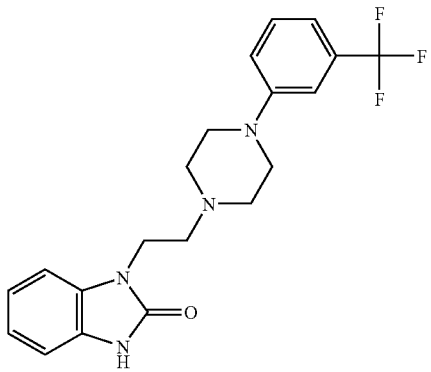 [SMILES: O=c1[nH]c2ccccc2n1CCN1CCN(c2cccc(C(F)(F)F)c2)CC1]

Flibanserin is a known post-synaptic full serotonin (5-$HT_{1A}$) agonist and 5-$HT_{2A}$ antagonist. It is therefore a promising therapeutic agent for the treatment of a variety of diseases, for instance depression, schizophrenia, and anxiety.

In acidic environment compounds such as flibanserin are usually very well water soluble whereas in neutral or basic environment these drugs can be practically insoluble. For example, flibanserin shows a solubility of 6.2 mg/ml in 0.1 N HCl and a solubility of 0.002 mg/ml in 0.05 M phosphate buffer pH 6.8. These physicochemical properties of basic compounds make it difficult to develop extended release dosage forms. There is a natural pH gradient from the acidity of the stomach where the pH of physiological fluids are typically around 1-2, through the weakly acidic duodenum to the virtually neutral environment of the small intestine where the pH is in the range of 5-8.

The drug release of flibanserin from conventional systems containing only pH-independent swelling polymers would be much faster in the stomach compared to the slower or even incomplete drug release in the small intestine and the colon. Formulations containing only pH-dependent retarding polymers would not allow for drug release over an extended period of time because these polymers loose their retarding effect above a certain pH. For example, Eudragit® L 100-55 forms an insoluble and impermeable film below pH 5.5, but dissolves above this pH, Carbomers form an insoluble barrier in the stomach but a more permeable gel layer in the intestine and alginic acids form an insoluble gel layer in acidic environment, but are converted to the soluble sodium alginates at a higher pH. As a result it is also difficult to find out functional excipients which would provide an improved bioavailability over the whole gastrointestinal tract for basic drugs with pH-dependent water solubility.

In prior art a number of approaches is described which provides release systems:

For example U.S. Pat. No. 4,792,452 describes a controlled release pharmaceutical formulation from which a pharmaceutical of a basic character is released at a controlled rate irrespective of the pH of the environment, consisting essentially of a pharmaceutical of a basic character, a pH-dependent polymer which is a salt of alginic acid, in an amount of from about 15 to about 45% by weight of the formulation, said salt of alginic acid having a viscosity of within the range from about 4 to about 500 centipoises in 1% solution at 25° C.; a pH-independent hydrocolloid gelling agent having a viscosity within the range of from about 50 to about 100,000 centipoises in 2% solution at 20° C., in an amount within the range of from about 3 to about 35% by weight of the formulation, and binder, whereby said formulation being free of calcium ion. The drug used is preferably a calcium channel blocker such as verapamil usually formulated in form of its hydrochloride.

As already explained after oral administration the alginates present in the controlled release pharmaceutical formulation are converted to alginic acid in the stomach and form an insoluble gel layer around the tablet particularly in the presence of calcium ions. Therefore, calcium ions are expressly excluded, which provides a very limited usability of the proposed formulation.

Furthermore, U.S. Pat. No. 4,968,508 is directed to a sustained release matrix formulation in tablet unit dosage form comprising from about 0.1% by weight to about 90% by weight of cefaclor, from about 5% by weight to about 29% by weight of a hydrophilic polymer, and from about 0.5% by weight to about 25% by weight of an acrylic polymer which dissolves at a pH in the range of about 5.0 to about 7.4, with the proviso that the total weight of the hydrophilic polymer and said acrylic polymer is less than 30% by weight of the formulation. The active substance is an antimicrobial agent, namely cefaclor, i.e. the proposed formulation is especially designed for zwitterions having both an acidic and a basic functional group having very specific requirements.

It is therefore an object of the present invention to provide an improved extended release pharmaceutical composition which avoids the disadvantages of the prior art and allows to provide a pH-independent release profile in order to improve the bioavailability of flibanserin. Furthermore a method of manufacturing the same shall be provided.

DESCRIPTION OF THE INVENTION

Surprisingly, it has been found that a specific combination of three functional excipients provides an extended release system having a pH-independent release profile for a pharmaceutical flibanserin formulation.

Therefore, the present invention provides a pharmaceutical extended release system, particularly for oral administration, of a pH-dependent water-soluble active substance, comprising or essentially consisting of
a) flibanserin or a pharmaceutically acceptable derivative thereof as active substance;
b) one or more pharmaceutically acceptable pH-dependent polymers;
c) one or more pharmaceutically acceptable pH-independent polymers;
d) one or more pharmaceutically acceptable acids; and
e) optionally one or more additives.

It is therefore provided an extended release system, particularly for oral administration, of flibanserin which guarantees largely pH-independent bioavailability of the active substance. Therefore, the extended release formulations of flibanserin of the present invention provide a pH-independent drug release behavior, particularly in the range from pH 1-5. These formulations contain organic acid(s) and a combination of pH-dependent as well as pH-independent retarding polymers as functional excipients.

The inventors of the present invention have found out that the proper combination of pH-dependent and pH-independent polymers can level out the effect of the decreasing solubility of the drug, particularly flibanserin, in the lower parts of the gastrointestinal tract while maintaining sufficiently slow release in the stomach. As a result, the difficulty to establish a suitable balance between the different parts of the gastrointestinal tract with different pH environment has been surprisingly managed.

Further, enhancement of drug release such as flibanserin in release media of elevated pH can be achieved by the addition of organic acid(s) which creates an acidic pH in the microenvironment within the extended release system and thus improves the solubility of the drug.

A "system" as used in the present invention should be understood in its broadest meaning comprising any type of formulation, preparation or pharmaceutical dosage form, which is particularly suitable for oral administration. The extended release system may be in form of a pellet, tablet, matrix tablet, bilayer tablet or mini tablet. The system may be administered directly, e.g. in form of a tablet, or may be filled in another dosage form such as a capsule. The extended release system according to the present invention is preferably provided in form of a tablet or a bilayer tablet.

In the context of the present invention the term "extended release" should be understood in contrast to "immediate release". The active ingredient is gradually, continuously liberated over time, sometimes slower or faster, but virtually independent from the pH value. In particular, the term indicates that the system does not release the full dose of the active ingredient immediately after oral dosing and that the formulation allows a reduction in dosing frequency.

The organic acids are not limited according to the frame of the present invention but any acid usable in pharmaceuticals may be employed. The organic acid is not necessarily used in the form of a solid or mixture of solids but it may be employed in form of a liquid or mixtures of liquids, for example, by firstly adhering or coating the organic acid onto a carrier or carrier particles. For instance, the adhering or coating can be carried out by a conventional coating method which is usually used in the manufacturing of pharmaceutical preparations, such as fluidized bed coating, pan coating, or the like. The inert carrier may include particles of a carrier substance, such as sucrose, lactose, starches, crystalline cellulose, colloidal silicon dioxide, and the like.

The pharmaceutically acceptable organic acids may be preferably selected from the group consisting of acetic acid, adipic acid, ascorbic acid, arginine, asparagines, aspartic acid, benzenesulphonic acid (besylate), benzoic acid, p-bromophenylsulphonic acid, camphorsulphonic acid, carbonic acid, gamma-carboxyglutamic acid, citric acid, cysteine, ethanesulphonic acid, fumaric acid, particularly cis-fumaric acid and/or trans-fumaric acid, gluconic acid, glutamic acid, glutaric acid, l-glutamine, hydrobromic acid, hydrochloric acid, hydroiodic acid, isethionic acid, isoleucine, lactic acid, l-leucine, lysine, maleic acid, malic acid, malonic acid, mandelic acid, methanesulphonic acid (mesylate), methionine, mucinic acid, nitric acid, ornithine, oxalic acid, pamoic acid, pantothenic acid, phosphoric acid, serine, succinic acid, sulphuric acid, tartaric acid, p-toluenesulphonic acid, tyrosine glutamic acid, valine and derivatives and mixtures thereof. The above listing is not intended to be of limitative character, the skilled person is familiar with further examples. Particularly preferred are adipic acid, ascorbic acid, aspartic acid, citric acid, fumaric acid, lactic acid, malic acid, succinic acid and tartaric acid, preferably succinic acid, tartaric acid and fumaric acid.

The organic acid(s) is (are) preferably present in an amount of 0.25-40% by weight, more preferably 0.5-35% by weight, most preferably 1-30% by weight, particularly 5-30% by weight.

It should be noted that the ranges of values given herein expressly include all the numerical values, both whole numbers and fractions, within the ranges as specified.

The pH-independent polymer is not limited according to the present invention; it may be used any pharmaceutically acceptable polymer which has a solubility characteristic being independent from the pH value of the environment.

The one or more pH-independent polymers of the present invention comprise alkylcelluloses, such as, methylcellulose, ethylcelluloses; hydroxyalkyl celluloses, for example, hydroxymethyl cellulose, hydroxyethyl cellulose, hydroxypropyl cellulose and hydroxybutyl cellulose; hydroxyalkyl alkylcelluloses, such as hydroxyethyl methylcellulose and hydroxypropyl methylcellulose; carboxyalkylcellulose esters; other natural, semi-synthetic, or synthetic di-, oligo- and polysaccharides such as galactomannans, tragacanth, agar, guar gum, and polyfructans; ammonio methacrylate copolymers; polyvinylalcohol; polyvinylpyrrolidone, copolymers of polyvinylpyrrolidone with vinyl acetate; combinations of polyvinylalcohol and polyvinylpyrrolidone; polyalkylene oxides such as polyethylene oxide and polypropylene oxide; copolymers of ethylene oxide and propylene oxide as well as derivatives and mixtures thereof; preferably cellulose ether derivatives such as hydroxypropyl methylcellulose and hydroxypropyl cellulose, most preferred hydroxypropyl methylcellulose, for example Methocel ethers.

The term "derivatives" according to the present invention is meant to include any compound derived from the mentioned compounds as basic system, for example by substitution with one or more functional groups. This belongs to the general knowledge of the skilled person.

The pH-independent polymer may be used alone or in combination of two or more pH-independent polymers. The pH-independent polymer(s) may be present in an amount of 0.5-75% by weight, preferably 1-70% by weight, more preferably 2-65% by weight, particularly 5-50% by weight and most preferably 15-30% by weight.

Also the pH-dependent polymer is not limited according to the present invention. Any pharmaceutically acceptable polymer may be used which has a pH-dependent solubility, preferably a polymer which has a high solubility in high pH medium and a low solubility in low pH medium in the sense that the solubility of the polymer is preferably better in high pH medium (pH about more than 4) compared with low pH medium (pH about 1-2).

The pH-dependent polymer(s) of the present invention comprises acrylic acid polymerisate, methacrylic acid copolymers, alginates, carrageenans, acacia, xanthan gum, chitin derivates such as chitosan, carmellose sodium, carmellose calcium, phthalate such as hydroxypropyl methyl cellulose phthalate, cellulose acetate phthalate, polyvinyl acetate phthalate, trimellitate such as cellulose acetate trimellitate, shellac and derivatives and mixtures thereof, preferably methacrylic acid copolymers such as poly(methacrylic acid, ethylacrylate) 1:1 (Eudragit® L 100-55), poly(methacrylic acid, methyl methacrylate) 1:1 (Eudragit® L 100), poly (methacrylic acid, methyl methacrylate) 1:2 (Eudragit® S), and alginates (such as Protanal®), most preferably used are Eudragit® L and Protanal®.

The pH-dependent polymer may be used alone or in combination of two or more pH-dependent polymers. The pH-dependent polymer(s) may be present in an amount of 0.25-25% by weight, more preferably 1-20% by weight, most preferably 2-15% by weight, particularly 3-10% by weight.

The term "one or more" or "at least one" as used in the present invention stands for 1, 2, 3, 4, 5, 6, 7, 8, 9, 10 compounds or even more. Preferred embodiments comprise 1, 2, or 3 such compounds. More preferred embodiments comprise 1 or 2 such compounds and even more preferred are embodiments comprising one of such compounds.

The pharmaceutically active substance which is contained in the extended release system of the present invention is flibanserin. Flibanserin can be used in form of the free base, or in form of any known pharmacologically acceptable derivative thereof such as its pharmaceutically acceptable acid addition salts and/or optionally in form of the hydrates and/or solvates thereof. Suitable acid addition salts include for example those of the acids selected from succinic acid, hydrobromic acid, acetic acid, fumaric acid, maleic acid, methanesulphonic acid, lactic acid, phosphoric acid, hydrochloric acid, sulphuric acid, tartaric acid and citric acid. Mixtures of the abovementioned acid addition salts may also be used. From the aforementioned acid addition salts the hydrochloride and the hydrobromide, particularly the hydrochloride, are preferred.

If flibanserin is used in form of the free base, it is preferably used in form of flibanserin polymorph A which represents the free base of flibanserin in a specific polymorphic form. Polymorph A and a process for its preparation are disclosed in WO 03/014079 A1, the whole disclosure thereof being incorporated by reference into the present specification.

Flibanserin is contained in an amount suitable for exhibiting the desired pharmacological activities of each medicament, which are known and varies in accordance with the type of medication. Flibanserin is preferably present in a pharmaceutically effective amount (0.01 mg to 200 mg, preferably from 0.1 to 100 mg or 0.1 to 50 mg), which, however, may depend from a number of factors for example the age and body weight of the patient, and the nature and stage of the disease. This is deemed to be within the capabilities of the skilled man, and the existing literature on the components can be consulted in order to arrive at the optimum dose. The dosis range applicable per day is between 0.1 to 400, preferably between 1.0 to 300, more preferably between 2 to 200 mg.

The dosage forms are administered to the patient 1, 2, 3, or 4 times daily. It is preferred that the formulations of the invention are administered either three or fewer times, more preferably once or twice daily consecutively over a period of time.

Preferably, the dose is administered to a patient in the morning and the evening, more preferably once in the morning (25 or 50 mg of flibanserin) and once in the evening (25 or 50 mg of flibanserin), most preferably once in the evening only (50 or 100 mg of flibanserin) consecutively over a period of time.

In the extended release system of the present invention the flibanserin content is preferably in an amount of not more than 50% by weight, more preferably not more than 45% by weight, most preferably not more than 40% by weight. The range is preferably from 2.5-50% by weight, preferably from 5-45% by weight, more preferably from 10-40% by weight and most preferably from 15-30% by weight.

The doses given above expressly include all the numerical values, both whole numbers and fractions, within the range specified.

The indication of flibanserin may include all known indications thereof, preferably in the treatment of patients suffering from central nervous system disorders, in particular in affective disorders (e.g. depression like major depressive disorder, childhood depression, dysthymia, seasonal affective disorder, dysthymic disorder and minor depressive disorder; bipolar disorders), anxiety (incl. panic disorder with or without agoraphobia, agoraphobia without history of panic disorder, specific phobia (simple phobia), social phobia (social anxiety disorder), obsessive-compulsive disorder (OCD), post-traumatic stress disorder, acute stress disorder, generalized anxiety disorder and anxiety disorder not otherwise specified), sleep and sexual disorders (e.g. Hyposexual Desire Disorder, premenstrual disorders like premenstrual dysphoria, premenstrual syndrome, premenstrual dysphoric disorder; sexual aversion disorder, sexual arousal disorder, orgasmic disorder, sexual pain disorders like dyspareunia, vaginismus, noncoital sexual pain disorder; sexual dysfunction due to a general medical condition and substance-induced sexual dysfunction), psychosis, schizophrenia (including the disorganized type, the catatonic type, the paranoid type, the undifferentiated type, the residual type of schizophrenia, schizoaffective disorder, schizophreniform disorder, delusional disorder, brief psychotic disorder, shared psychotic disorder, psychotic disorder due to a general medical condition, substance-induced psychotic disorder, and psychotic disorder not otherwise specified), personality disorders, mental organic disorders, mental disorders in childhood, aggressiveness, age associated memory impairment, for neuroprotection, the treatment and/or prevention of neurodegenerative diseases as well as cerebral ischaemia of various origins (e.g. epilepsy, hypoglycaemia, hypoxia, anoxia, brain trauma, brain oedema, amyotropic lateral sclerosis, Huntington's disease, Alzheimer's disease, hypotension, cardiac infarct, brain pressure (elevated intracranial pressure), ischaemic and haemorrhagic stroke (stroke), global cerebral ischaemia during stoppage of the heart, diabetic polyneuropathy, tinnitus, perinatal asphyxia, cardiac hypertrophia (thickening of the heart muscle) and cardiac insufficiency (weakness of the heart muscle); anorexia nervosa (incl. binge-eating/purging type of anorexia nervosa and the restricting type of anorexia nervosa), Attention Deficit Hyperactivity Disorder (ADHD) (incl. ADHD predominantly combined type, ADHD predominantly inattentive type, and ADHD predominantly hyperactive-impulsive type), obesity (incl. exogenic obesity, hyperinsulinaemic obesity, hyperplasmic obesity, hyperphyseal adiposity, hypoplasmic obesity, hypothyroid obesity, hypothalamic obesity, symptomatic obesity, infantile obesity, upper body obesity, alimentary obesity, hypogonadal obesity and central obesity), urinary incontinence (incl. overactive bladder syndrome, urgency, urge urinary incontinence, stress urinary incontinence, mixed urinary incontinence), chronic pain (incl. neuropathic pain, diabetic neuropathy, post-herpetic neuralgia (PHN), carpal tunnel syndrome (CTS), HIV neuropathy, phantom limb pain, complex regional pain syndrome (CPRS), trigeminal neuralgia/trigeminus neuralgia/tic douloureux, surgical intervention (e.g. post-operative analgesics), diabetic vasculopathy, capillary resistance or diabetic symptoms associated with insulitis, pain associated with angina, pain associated with menstruation, pain associated with cancer, dental pain, headache, migraine, trigeminal neuralgia, temporomandibular joint syndrome, myofascial pain muscular injury, fibromyalgia syndrome, bone and joint pain (osteoarthritis), rheumatoid arthritis, rheumatoid arthritis and edema resulting from trauma associated with burns, sprains or fracture bone pain due to osteoarthritis, osteoporosis, bone metastases or unknown reasons, gout, fibrositis, myofascial pain, thoracic outlet syndromes, upper back pain or lower back pain (wherein the back pain results from systematic, regional, or primary spine disease (radiculopathy), pelvic pain, cardiac chest pain, non-cardiac chest pain, spinal cord injury (SCI)-associated pain, central post-stroke pain, cancer neuropathy, AIDS pain, sickle cell pain and geriatric pain), Valvular Heart Disease (incl. valvular stenosis, valvular regurgitation, atresia of one of the valves, mitral valve prolapse).

The selection of polymers, at least one pH-dependent and at least one pH-independent, have an influence on the release of the flibanserin in order to establish the desired release profiles. Although the active substance present has a pH-dependent solubility the release profile of the extended release system according to the present invention is almost independent from the pH value resulting in an improved bioavailability. In fact, the combination of different retarding polymers and the addition of organic acid(s) lead to a widely pH-independent drug release (in the range of pH 1-5) of the pH-dependent water soluble flibanserin.

Therefore, the aforementioned extended release system of the present invention comprises or essentially consists of flibanserin, pH-dependent and pH-independent retarding polymers, organic acid(s), optionally in combination with additives suitable in pharmaceutical formulations such as excipients, carriers, technological adjuvants and the like. Preferred additives are for example fillers, lubricants, glidants, solubilizers, dyes, binders and the like.

According to a preferred embodiment the extended release system of the present invention consists of

| | |
|---|---|
| flibanserin or a pharmaceutically acceptable derivative thereof | 5-50% by weight |
| pH-dependent polymer(s) | 0.25-25% by weight |
| pH-independent polymer(s) | 0.5-75% by weight |
| organic acid(s) | 0.25-40% by weight |
| lubricant(s) | 0.1-4% by weight |
| additional additives | ad 100% by weight |

According to a more preferred embodiment the extended release system of the present invention consists of

| | |
|---|---|
| flibanserin or a pharmaceutically acceptable derivative thereof | 5-50% by weight |
| pH-dependent polymer(s) | 1-20% by weight |
| pH-independent polymer(s) | 1-70% by weight |
| organic acid(s) | 0.5-35% by weight |
| lubricant(s) | 0.2-3.5% by weight |
| additional additives | ad 100% by weight |

According to an even more preferred embodiment the extended release system of the present invention consists of

| | |
|---|---|
| flibanserin or a pharmaceutically acceptable derivative thereof | 5-50% by weight |
| pH-dependent polymer(s) | 2-15% by weight |
| pH-independent polymer(s) | 2-65% by weight |
| organic acid(s) | 1-30% by weight |
| lubricant(s) | 0.25-3% by weight |
| additional additives | ad 100% by weight |

According to an even more preferred embodiment the extended release system of the present invention consists of

| | |
|---|---|
| flibanserin or a pharmaceutically acceptable derivative thereof | 5-50% by weight |
| pH-dependent polymer(s) | 3-10% by weight |
| pH-independent polymer(s) | 5-50% by weight |
| organic acid(s) | 5-30% by weight |
| lubricant(s) | 1-3% by weight |
| additional additives | ad 100% by weight |

According to a particularly preferred embodiment the extended release system of the present invention consists of

| | |
|---|---|
| flibanserin or a pharmaceutically acceptable derivative thereof | 5-50% by weight |
| pH-dependent polymer(s) | 3-10% by weight |
| pH-independent polymer(s) | 15-30% by weight |
| organic acid(s) | 5-30% by weight |
| lubricant(s) | 1-3% by weight |
| additional additives | ad 100% by weight |

Unless otherwise stated, percentages specified are always percent by weight.

Therefore, additives e.g. excipients, carriers, technological adjuvants may be present such as lubricants, glidants, granulating agents, anti-caking agents, agglomeration inhibitors, antiadherents, anti-tacking agent, anti-sticking agent, flavors, aromatiziers, dyes or colorants, preservatives, plastizers, wetting agents, sweeteners, chelating agents, stabilizers, solubilizers, antioxidants, fillers, diluents and the like. These pharmaceutically acceptable formulating agents are e.g. present in order to promote the manufacture, compressibility, appearance and/or taste of the preparation. Other conventional additives known in the art can also be included. The above listing is not intended to be of limitative character, the skilled person is familiar with further examples.

A lubricant or agglomeration inhibitor can be used to enhance release of the dosage form from the apparatus on which it is formed, for example by preventing adherence to the surface of an upper punch ("picking") or lower punch ("sticking"). These materials may also possess antiadherent or glidant properties. Preferable lubricants are for example stearic acid as well as salts thereof including sodium stearate, calcium stearate, zinc stearate, magnesium stearate, glyceryl monostearate, glyceryl palmitostearate, polyoxyl-40-stearate, particularly magnesium stearate, polyethylene glycols (all types at different molecular weights of PEGs), fumaric acid, glycerides such as glyceryl behenate (Compritol® 888), Dynasan® 118 or Boeson® VP. Others includes DL-leucine, magnesium silicate, calcium silicate, magnesium trisilicate, talc, starch, tribasic calcium phosphate, magnesium oxide, mineral oil, poloxamer, polyvinyl alcohol, hydrogenated oils, such as hydrogenated vegetable oils (e.g. Sterotex®), hydrogenated castor oil, kaolin, (light) mineral oil, canola oil, triglycerides, such as medium-chain triglycerides, myristic acid, palmitic acid, polyethylene glycols (all types at different molecular weights of PEGs), tribasic calcium phosphate, benzoate such as sodium or potassium benzoate, sodium benzoate, sodium chloride, sodium lauryl sulfate, magnesium lauryl sulphate, sodium acetate, fumaric acid and fumarate such as sodium fumarate, sodium stearyl fumarate, sodium oleate, waxes and derivatives and mixtures thereof.

An anti-tacking agent, anti-sticking agent or glidant or an agent to improve flowability can be used to improve powder flow properties prior to and during the manufacturing process and to reduce caking. Among this group of excipients may be exemplarily mentioned silicon dioxide, particularly colloidal silicon dioxide (e.g. Aerosil®, Cab-O-Sil®), stearic acid as well as salts thereof including sodium stearate, calcium stearate, zinc stearate, magnesium stearate, magnesium silicate, calcium silicate, magnesium trisilicate and talc. Preferably glidants are colloidal silicon dioxide and talc.

As binder, it is possible to use any binder usually employed in pharmaceuticals. Exemplarily mentioned are naturally occurring or partially or totally synthetic polymers selected from acacia, agar, alginic acid, carbomers, carmellose sodium, carrageenan, cellulose acetate phthalate, ceratonia, chitosan, confectionar's sugar, copovidone, povidone, cottonseed oil, dextrate, dextrin, dextrose, polydextrose, maltodextrin, maltose, cellulose and derivatives thereof such as microcrystalline cellulose, methylcellulose, ethylcellulose, hydroxyethyl cellulose, hydroxyethyl methylcellulose, hydroxypropyl celluloses, carboxymethylcelluloses, hypromelloses (cellulose hydroxypropyl methyl ether), starch and derivatives thereof, such as pregelatinized starch, hydroxypropylstarch, corn starch, gelatin, glyceryl behenate, tragacanth, guar gum, hydrogenated vegetable oils, inulin, lactose, glucose, magnesium aluminium silicate, poloxamer, polycarbophils, polyethylene oxide, polyvinylpyrrolidone, copolymers of N-vinylpyrrolidone and vinyl acetate, polymethacrylates, polyethylene glycols, alginates such as sodium alginate, gelatin, sucrose, sunflower oil, zein as well as derivatives and mixtures thereof.

Particularly preferred binders are acacia, hydroxypropyl celluloses, hydroxypropyl methylcelluloses, methylcelluloses, hydroxyethyl celluloses, carboxymethylcelluloses, polyvinylpyrrolidone, the copolymers of N-vinylpyrrolidone and vinyl acetate, or combinations of these polymers. The above listing is not intended to be of limitative character, the skilled person is familiar with further examples.

As further additives which may be present the following non limitative groups are given
  preservatives, preferably antimicrobial preservatives such as benzalkonium chloride, benzoic acid, methyl parahydroxybenzoate, propyl parahydroxybenzoate, sodium benzoate and sorbic acid;
  sweetening agents such as acesulfame potassium, alitame, aspartame, compressible sugar, confectioner's sugar, dextrose, erythritol, fructose, glycerin, inulin, isomalt, lactitol, liquid glucose, maltitol, maltitol solution, maltose, mannitol, neospheridin dihydrochalcone, polydextrose, saccharin, saccharin sodium, sodium cyclamate, sorbitol, sucralose, sucrose, thaumatin, trehalose, xylitol;
  solubilizers such as benzalkonium chloride, benzethonium chloride, benzyl alcohol, benzyl benzoate, cetylpyridinium chloride, cyclodextrins, lecithin, meglumine, poloxamers, polyethylene alkyl ethers, polyoxyethylene alkyl ethers, polyoxyethylene castor oil derivatives, polyoxyethylen sorbitan fatty acid esters, polyoxyethylene stearates, povidone, 2-pyrrolidone, sodium bicarbonate, sorbitan esters, stearic acid, sulfobutylether β-cyclodextrin, sodium dodecyl sulphate (SDS) and vitamin E-TPGS;
  separating agents such as e.g. talc, magnesium stearate or silicic acid serves to prevent the particles from aggregating during the manufacturing process; and
  plasticizers are preferably not present in the extended release system which is usually free of plasticizer; however in some rare cases the plasticizers may be selected from e.g. citrates such as acetyltributyl citrate, acetyltriethyl citrate, tributyl citrate, triethyl citrate, benzyl benzoate, castor oil, phthalates such as cellulose acetate phthalate, dibutyl phthalate, diethyl phthalate, dimethyl phthalate, hypromellose phthalate, polyvinyl acetate phthalate, dimeticon, fractionated coconut oil, chlorbutanol, dextrin, sebacate such as dibutyl sebacate, glycerin, glycerin derivatives such as glycerol monostearate, glycerol triacetate (triacetin), acetylated monoglyceride, mannitol, mineral oil, lanolin alcohols, palimitic acid, 2-pyrrolidone, sorbitol, stearic acid, triethanolamin, polyethyleneglycols (all types at different molecular weights of PEGs), and propylene glycol, and derivatives and mixtures thereof,
  pigments which are especially useful are titanium dioxide, indigo carmine, iron oxide pigments such as iron oxides red and yellow, and some of the aluminium lakes as well as pigment black, pigment white, pigment yellow, sunset yellow, sunset yellow lake, quinoline yellow lake and the like.

The oral formulation of the present inventions additionally comprises one or more excipient(s) with diluting or filling properties (fillers or diluents). Fillers or diluents are inert compounds designed to make up the required bulk of the dosage form when the drug dosage itself is inadequate to produce this bulk.

Suitable fillers or diluents may be selected from, for example, lactose, in particular lactose monohydrate, talc, starches and derivatives such as pregelatinized starch, corn starch, wheat starch, rice starch, potato starch, sterilizable maize, sodium chloride, calcium carbonate, calcium phosphate, particularly dibasic calcium phosphate, calcium sulphate, dicalcium or tricalcium phosphate, magnesium carbonate, magnesium oxide, cellulose and derivatives, such as powdered cellulose, microcrystalline or silicified microcrystalline cellulose, cellulose acetate, sugars and derivatives such as confectioner's sugar, fructose, sucrose, dextrates, dextrin, D-sorbitol sulfobutylether 9-cyclodextrin, dextrose, polydextrose, trehalose, maltose, maltitol, mannitol, maltodextrin, sorbitol, inulin, xylitol, erythritol, isomalt, kaolin and lactitol.

Possible chelating agents which may be added are edetic acid, dipotassium edetate, disodium edetate, edetate calcium disoidium, trisodium edetate, maltol and the like.

It is a matter of course that an additive may have more than one functionality so that they may be categorized among more than one type of additive. For example corn starch or pregelatinized starch may impart several functions at the same time such as swelling polymer, filler, glidant, and the like. However, the skilled person knows the several functions and is able to select the additive according to the intended use thereof.

The resulting extended release system may finally be coated with a coating preferably of a pharmaceutically conventional film forming agent, and optionally additives. This may be done by conventional methods. Coating serves to mask the taste of the drug, make e.g. a tablet easier to swallow, to reduce any increased abrasion during packing, e.g. into capsules, to increase the shelf life and/or as further diffusion barrier, in some cases, it may improve the appearance of the dosage form.

The extended release system can be sugar coated according to procedures well known in the art, or can be coated with any one of numerous polymeric film-forming agents frequently employed by formulation chemists. Suitable film-forming agents include for example ammonium alginate, chitosan, chlorpheniramine maleate, copovidone, phthalate such as dibutyl phthalate, diethyl phthalate, dimethyl phthalate, cellulose acetate phthalate, polyvinyl acetate phthalate, dibutyl sebacate, ethyl lactate, alkylcelluloses and derivatives thereof such as ethylcelluloses, methylcelluloses, gelatin, hydroxyalkyl celluloses and derivatives thereof such as hydroxyethyl cellulose, hydroxypropyl cellulose, hydroxyalkyl alkylcellulose and derivatives thereof such as hypromelloses (hydroxypropyl methylcellulose), hydroxypropyl methylcellulose acetate succinate, hydroxypropyl methylcellulose phthalate, cellulose acetate trimellitate, cellulose acetate phthalate, maltodextrin, calcium carbonate, polydextrose, polyethylene glycols (all types at different molecular weights of PEGs), polyethylene oxide, polymers and copolymers of acrylic and methacrylic acid and the esters thereof, or combinations of these polymers such as polymethacrylates, poly(methylvinyl ether/maleic anhydride), polyvinyl acetate phthalate, triethyl citrate, vanillin, shellac as well as derivatives and mixtures thereof.

Particularly preferred film-forming agents are hydroxypropyl cellulose, hydroxypropyl methylcellulose, methylcelluloses, polymers and copolymers of acrylic and methacrylic acid and the esters thereof, or combinations of these polymers. Preferably polymers are poly(methacrylic acid, ethylacrylate) 1:1 (Eudragit® L 100-55 or Eudragit® L 30D-55); poly(methacrylic acid, methyl methacrylate) 1:1 (Eudragit® L 100); poly(methacrylic acid, methyl methacrylate) 1:2 (Eudragit® S); hydroxypropyl methylcellulose acetate succinate, hydroxypropyl methylcellulose phthalate, cellulose acetate trimellitate, cellulose acetate phthalate (Aquacoate® CPD), polyvinyl acetate phthalate (Sureteric®), and shellac.

Further suitable additives, excipients, diluents, carriers, technological adjuvants, if desired, may be present.

The present extended release system of the present invention may be prepared by methods which are well known to those skilled in the art, for example wet granulation, direct compression or roller compaction process can be applied to the manufacturing of the extended release system. The roller compaction process is particularly preferred.

The pH-dependent polymer employed in the present extended release system may be incorporated into the formulation at different stages in the process. The pH-independent polymer may be added, for example in form of a finely divided powder, to the active substance and a part or all of the pH-dependent polymer along with suitable excipients or additives as desired. Then, the ingredients may be thoroughly mixed to obtain a pre-mixture which is subsequently subjected to a compacting in a suitable apparatus. Thereafter further powdery additives may be added and sieved to obtain a final mixture from which e.g. a tablet may be pressed.

Alternatively, all or a part of the pH-dependent polymer may also be added after the pre-mixture has been obtained and/or after compaction have been completed. The skilled person is readily able to produce a formulation without undue burden.

It is also possible to have a bilayer tablet with one immediate release layer and one extended release layer of Flibanserin.

Thus, subject of the present invention is an oral to take pharmaceutical extended release system, in particular tablets, like tablets for swallowing, bilayer tablets, sugar-coated tablets, coated tablets, chewable tablets, matrix tablets, pills or capsules. Among these tablets are most preferred according to the present invention. Among the latter coated tablets and/or swallowable tablets are preferred.

The extended release system of the present invention can be of any suitable size and shape, for example round, oval, polygonal or pillow-shaped, and optionally bear non-functional surface markings.

If the formulation which is subject of the present invention is a tablet, preferably it shall have a round or oval shape. The size thereof preferably shall be between 5 mm and 12 mm diameter in case of round shape and between 6×12 mm and 10×20 mm in case of oval shape. The weight thereof preferably shall be between 50 and 1000 mg If the formulation which is subject of the present invention is a capsule, preferably it shall be of the capsule size of between 5 and 0. The capsule then comprises the pharmaceutical extended releases system in form of granules which correspond in their chemical and physical composition to the core of the tablet but which are smaller in size.

The tablets of the present invention or capsules may be packed in bottles or blisters well known in the art. Among such blisters are such being made of polyvinylchloride or polyvinylidene chloride. Aluminum-blisters are also possible. Bottles may be made of poylpropylene or polyethylene for example. Optionally desiccants like silica gel or molecular sieves can be used in the bottles. Other conventional packaging materials are possible, too.

The extended release systems of the invention can be packaged in a container, accompanied by a package insert providing pertinent information such as, for example, dosage and administration information, contraindications, precautions, drug interactions and adverse reactions.

BRIEF DESCRIPTION OF THE DRAWINGS

In the drawings

FIG. 1 shows a schematic illustration of a preferred embodiment of the extended release system of the present invention, wherein the dosage form comprises or essentially consists of the active substance in form of flibanserin 20, at least one pH-dependent polymer 10, one or more pH modifier in form of at least one organic acid 30, and at least one pH-independent polymer 40. For the sake of clarity additives are omitted in FIG. 1. The extended release system according to the present invention may be considered to be a matrix type system which may be defined as well-mixed composite of ingredients fixed into a defined shape, preferably by tabletting. This intimate admixture of ingredients provides extended release of the active agent flibanserin 20 contained therein, although the pH value of the environment changes following administration.

FIGS. 2a and 2b show the function of a preferred embodiment of the extended release system of the present invention in schematic form after oral administration. FIG. 2a illustrates a low pH medium such as the environment in the stomach (pH about 1.2) and FIG. 2b illustrates a higher pH medium such as in the small intestine (pH 5-8), duodenum (pH 4-6.4), jejunum (pH 4-6.5) ileum (pH 6.5-8) and colon (pH 6-7.5).

"D" represents the diffusion layer and "DS" the drug substance, in the present case flibanserin. Usually, there exist two general flow directions, on one hand that of the aqueous medium, i.e. gastrointestinal juice, which diffuses into the extended release system of the present invention and on the other hand that of the drug substance which diffuses out of the extended release system. The dissolution of the drug substance is usually a function of the matrix porosity ($\epsilon$) and the drug substance solubility (L). If the matrix porosity and the solubility of the drug substance are raised the dissolution of the drug substance will increase.

Figure 1:
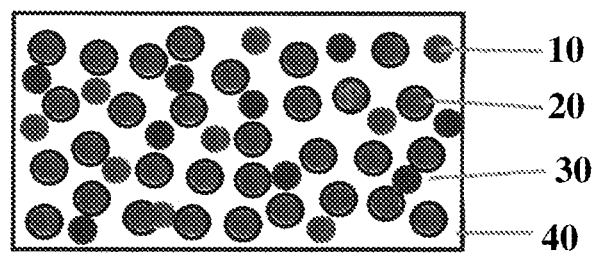
FIG. 1 shows a schematic illustration of a preferred embodiment of the extended release system according to the present invention.
Figure 2A:
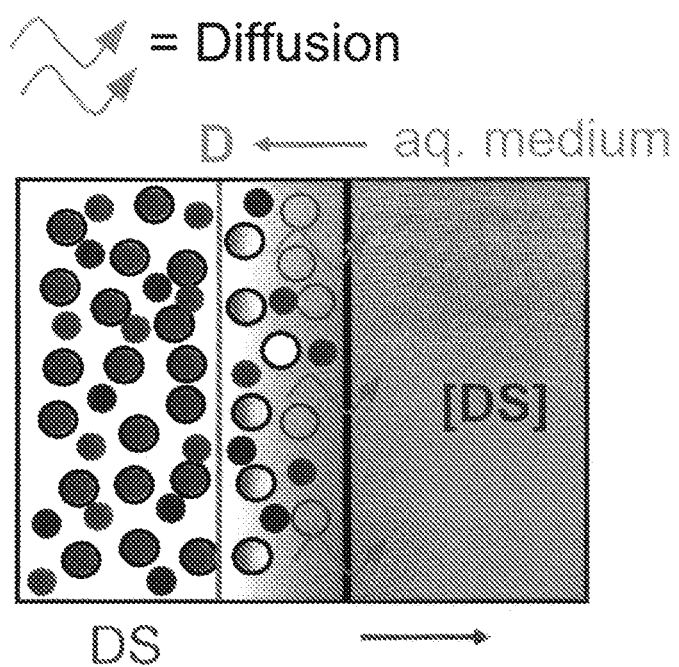
FIGS. 2a and 2b show the function of a preferred embodiment of the extended release system according to the present invention in schematic form.

In a low or acidic pH medium as shown in FIG. 2a (e.g. stomach) there exists a high solubility of the drug substance present so that a low porosity is desired. The pH-dependent polymer is insoluble in a low pH and represents a diffusion barrier for the aqueous media and the drug substance. The pH modifier being present is of less effectivity in an acidic pH medium.

Figure 2B:
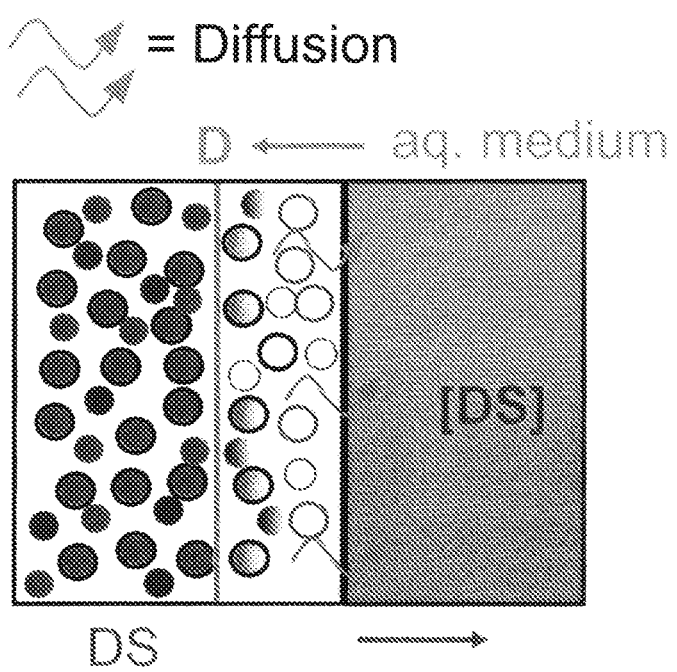

A higher pH medium as shown in FIG. 2b (e.g. intestine) provides a low solubility of the drug substance flibanserin. Therefore, the pH-dependent polymer which is soluble in the higher pH medium leads to a high porosity of the matrix system so that the release of the drug substance will be increased. Additionally the acid present supports the dissolution of the drug substance.

Therefore, the usual release capability of the aforementioned extended release matrix system is changed in such a manner to arrive at a practically independent pH release of the pH dependent soluble drug substance.

Figure 3:
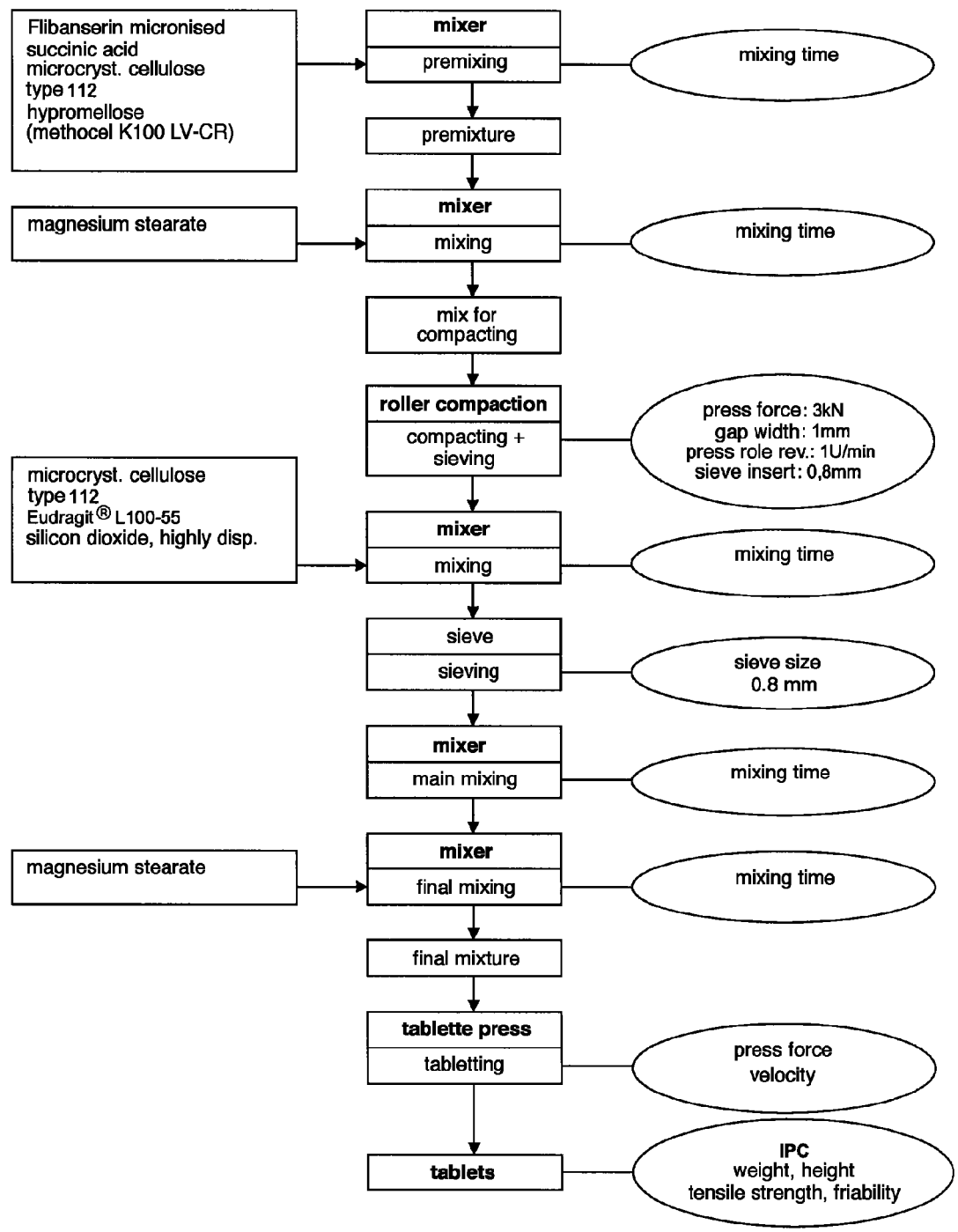
FIG. 3 represents a flow diagram illustrating a preferred method for the manufacturing of a preferred embodiment of the extended release system according to the present invention.

FIG. 3 will be described in detail in the Examples.

Figure 4:
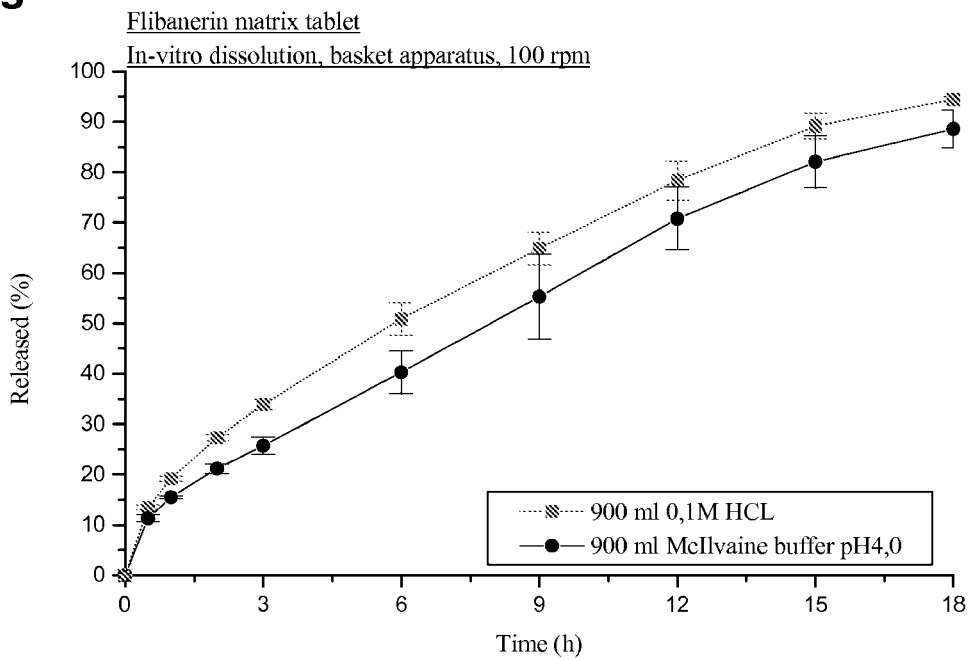
FIGS. 4 and 5 show in-vitro dissolution profiles of formulations according to the present invention

FIG. 4 shows in-vitro dissolution testing of example 1b conducted according to United States Pharmacopeia (USP) 28, chapter 711, using the same conditions and settings except for the composition and pH of the dissolution medium, which was varied between pH 1 and 4. Samples were taken after 0.5, 1, 2, 3, 6, 9, 12, 15 and 18 hours. In result, the average amount of drug released was comparable in both dissolution media at all time points.

Figure 5:
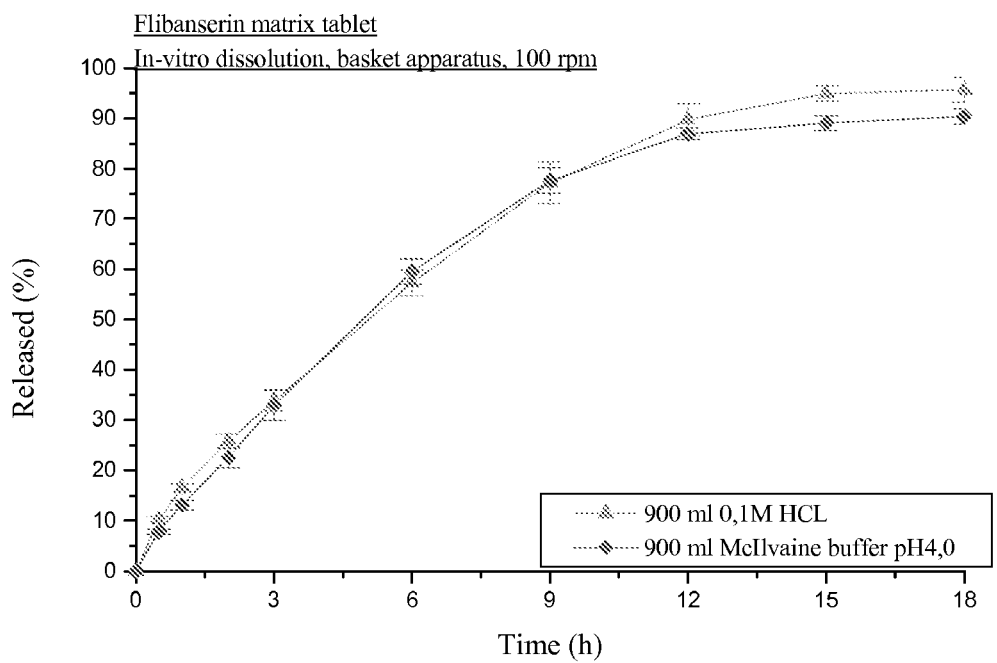

FIG. 5 shows in-vitro dissolution testing of example 1e conducted according to United States Pharmacopeia (USP) 28, chapter 711, using the same conditions and settings except for the composition and pH of the dissolution medium, which was varied between pH 1 and 4. Samples were taken after 0.5, 1, 2, 3, 6, 9, 12, 15 and 18 hours. In result, the average amount of drug released was comparable in both dissolution media at all time points.

The advantages of the present invention are manifold:

The extended release system according to the present invention is able to suppress the immediate dissolution and release of the active substance in acidic environment whereas the continuous release of the active substance in intestinal fluids can be reliably achieved. The desired blood level of the active substance can be realized for a long period of time.

The extended release system of the present invention remains sufficiently stable when stored. Only after the administration of the formulation system does the pH modifier dissolve and produce a micro climate in which the active substance can dissolve.

According to the present invention it is provided a virtually pH-independent release for the active substance flibanserin which is a weak base and which in the range from pH 1 to pH 7.5 would exhibit pH-dependent solubility characteristics. That is flibanserin usually has greater solubility under acidic conditions and lesser solubility under neutral and basic conditions. As a result the present invention provides a change of the release characteristics of flibanserin resulting in a significantly improved bioavailability which is independent on the pH in the gastrointestinal tract when administered orally.

The invention described will now be illustrated by the following Examples. However, it is expressly pointed out that the Examples and description are intended solely as an illustration and should not be regarded as restricting the invention.

EXAMPLE 1

In the following a preferably process to manufacture the extended release system of the present invention is exemplarily described. However, the process steps are not intended to be of limitative character at all.

The following process steps are illustrated in the flow chart shown in FIG. 3.

The preparation of the extended release system of the present invention in the following Example usually takes place over 7 steps:

step 1): preparation of the pre-mixture;
step 2): preparation of the mixture for compaction;
step 3): performing roller compaction;
step 4): preparation of the admixture;
step 5): preparation of the main mixture;
step 6): preparation of the final mixture; and
step 7): preparation of the tablets.

The steps will be described in the following in detail:

1. Pre-Mixture

To active substance flibanserin (200.00 g) pre-sieved (sieve size 0.5 mm) succinic acid (100.00 g), hypromellose (200.00 g) and microcrystalline cellulose (215.00 g) are added and mixed in a usual blender or mixer for 5 minutes.

2. Mixture for Compaction

To the pre-mixture obtained in above step 1 pre-sieved (sieve size 0.5 mm) magnesium stearate of herbal origin (5.00 g) is added and blended in a usual blender or mixer for 3 minutes.

3. Roller Compaction

The mixture obtained in above step 2 is subjected to a roller compaction process step as known to the skilled in the art.

4. Admixture

To the compacted mixture obtained in step 3, microcrystalline cellulose (215.00 g), Eudragit® L 100-55 (50.00 g) and highly disperse silicon dioxide (pre-sieved, sieve size 0.5 mm; 5.00 g) are added and blended for 5 minutes. Subsequently the obtained mixture is sieved (sieve size 0.8 mm).

5. Main Mixture

The admixture obtained in step 4 is again blended for further 5 minutes.

6. Final Mixture

To the main mixture obtained above in step 5 pre-sieved (sieve size 0.5 mm) magnesium stearate of herbal origin (10.00 g) is added and blended for 3 minutes.

7. Tablets

In a suitable tablet pressing apparatus the final mixture as obtained above in step 6 is pressed to obtain the desired tablets. In Process Controls (IPC) are employed as usual.

According to the aforementioned process the following tablets may be prepared:

EXAMPLE 1a

| Ingredient | [mg/tablet] |
| --- | --- |
| Flibanserin, micronised | 100.000 |
| Hydroxypropylcellulose | 100.000 |
| Microcrystalline cellulose | 215.000 |
| Succinic acid | 50.000 |
| Methacrylic acid - ethyl acrylate copolymer (1:1) | 25.000 |
| Silica, colloidal anhydrous | 2.500 |
| Magnesium stearate | 7.500 |
| Total | 500.000 |

EXAMPLE 1b

| Ingredient | [mg/tablet] |
| --- | --- |
| Flibanserin, micronised | 100.000 |
| Hypromellose 2208 | 100.000 |
| Microcrystalline cellulose | 215.000 |
| Succinic acid | 50.000 |
| Methacrylic acid - ethyl acrylate copolymer (1:1) | 25.000 |
| Silica, colloidal anhydrous | 2.500 |
| Magnesium stearate | 7.500 |
| Total | 500.000 |

EXAMPLE 1c

| Ingredient | [mg/tablet] |
| --- | --- |
| Flibanserin, micronised | 100.000 |
| Hypromellose 2208 | 100.000 |
| Microcrystalline cellulose | 115.000 |
| Tartaric acid | 100.000 |
| Fumaric acid | 50.000 |
| Methacrylic acid - ethyl acrylate copolymer (1:1) | 25.000 |
| Silica, colloidal anhydrous | 2.500 |
| Magnesium stearate | 7.500 |
| Total | 500.000 |

EXAMPLE 1d

| Ingredient | [mg/tablet] |
| --- | --- |
| Flibanserin, micronised | 100.000 |
| Hydroxypropylcellulose | 100.000 |
| Microcrystalline cellulose | 115.000 |
| Tartaric acid | 100.000 |
| Fumaric acid | 50.000 |
| Methacrylic acid - ethyl acrylate copolymer (1:1) | 25.000 |
| Silica, colloidal anhydrous | 2.500 |
| Magnesium stearate | 7.500 |
| Total | 500.000 |

EXAMPLE 1e

| Ingredient | [mg/tablet] |
| --- | --- |
| Flibanserin, micronised | 100.000 |
| Hydroxypropylcellulose | 100.000 |
| Hypromellose 2208 | 50.000 |
| Microcrystalline cellulose | 165.000 |
| Succinic acid | 50.000 |
| Methacrylic acid - ethyl acrylate copolymer (1:1) | 25.000 |
| Silica, colloidal anhydrous | 2.500 |
| Magnesium stearate | 7.500 |
| Total | 500.000 |

EXAMPLE 1f

| Ingredient | [mg/tablet] |
| --- | --- |
| Flibanserin, micronised | 100.000 |
| Hypromellose 2208 | 100.000 |
| Microcrystalline cellulose | 115.000 |
| Lactose monohydrate | 100.000 |
| Succinic acid | 50.000 |
| Methacrylic acid - ethyl acrylate copolymer (1:1) | 25.000 |
| Silica, colloidal anhydrous | 2.500 |
| Magnesium stearate | 7.500 |
| Total | 500.000 |

EXAMPLE 1g

| Ingredient | [mg/tablet] |
| --- | --- |
| Flibanserin, micronised | 100.000 |
| Hypromellose 2910 | 200.000 |
| Microcrystalline cellulose | 90.000 |
| Succinic acid | 50.000 |
| Carbomer 941 | 50.000 |
| Silica, colloidal anhydrous | 2.500 |
| Magnesium stearate | 7.500 |
| Total | 500.000 |

EXAMPLE 1h

| Ingredient | [mg/tablet] |
|---|---|
| Flibanserin, micronised | 100.000 |
| Hydroxypropylcellulose | 200.000 |
| Microcrystalline cellulose | 90.000 |
| Succinic acid | 50.000 |
| Carbomer 941 | 50.000 |
| Silica, colloidal anhydrous | 2.500 |
| Magnesium stearate | 7.500 |
| Total | 500.000 |

EXAMPLE 1i

| Ingredient | [mg/tablet] |
|---|---|
| Flibanserin, micronised | 100.000 |
| Hypromellose 2910 | 100.000 |
| Hydroxypropylcellulose | 100.000 |
| Microcrystalline cellulose | 90.000 |
| Succinic acid | 50.000 |
| Methacrylic acid - ethyl acrylate copolymer (1:1) | 50.000 |
| Silica, colloidal anhydrous | 2.500 |
| Magnesium stearate | 7.500 |
| Total | 500.000 |

EXAMPLE 1j

| Ingredient | [mg/tablet] |
|---|---|
| Flibanserin, micronised | 100.000 |
| Hypromellose 2208 | 100.000 |
| Microcrystalline cellulose | 215.000 |
| Succinic acid | 50.000 |
| Sodium alginate | 25.000 |
| Silica, colloidal anhydrous | 2.500 |
| Magnesium stearate | 7.500 |
| Total | 500.000 |

EXAMPLE 1k

| Ingredient | [mg/tablet] |
|---|---|
| Flibanserin, micronised | 100.000 |
| Hydroxypropylcellulose | 85.000 |
| Hypromellose 2208 | 42.500 |
| Microcrystalline cellulose | 117.750 |
| Succinic acid | 50.000 |
| Methacrylic acid - ethyl acrylate copolymer (1:1) | 21.250 |
| Silica, colloidal anhydrous | 2.125 |
| Magnesium stearate | 6.375 |
| Total | 425.000 |

EXAMPLE 1l

| Ingredient | [mg/tablet] |
|---|---|
| Flibanserin, micronised | 100.000 |
| Hydroxypropylcellulose | 85.000 |
| Methylcellulose | 42.500 |
| Microcrystalline cellulose | 117.750 |
| Succinic acid | 50.000 |
| Methacrylic acid - ethyl acrylate copolymer (1:1) | 21.250 |
| Silica, colloidal anhydrous | 2.125 |
| Magnesium stearate | 6.375 |
| Total | 425.000 |

EXAMPLE 1m

| Ingredient | [mg/tablet] |
|---|---|
| Flibanserin, micronised | 100.000 |
| Hydroxypropylcellulose | 85.000 |
| Methylcellulose | 42.500 |
| Microcrystalline cellulose | 117.750 |
| Tartaric acid | 50.000 |
| Methacrylic acid - ethyl acrylate copolymer (1:1) | 21.250 |
| Silica, colloidal anhydrous | 2.125 |
| Magnesium stearate | 6.375 |
| Total | 425.000 |

EXAMPLE 1n

| Ingredient | [mg/tablet] |
|---|---|
| Flibanserin, micronised | 100.000 |
| Hydroxypropylcellulose | 85.000 |
| Hypromellose 2208 | 42.500 |
| Microcrystalline cellulose | 117.750 |
| Tartaric acid | 50.000 |
| Methacrylic acid - ethyl acrylate copolymer (1:1) | 21.250 |
| Silica, colloidal anhydrous | 2.125 |
| Magnesium stearate | 6.375 |
| Total | 425.000 |

EXAMPLE 1o

| Ingredient | [mg/tablet] |
|---|---|
| Flibanserin, micronised | 75.000 |
| Hypromellose 2208 | 75.000 |
| Microcrystalline cellulose | 161.250 |
| Succinic acid | 37.500 |
| Methacrylic acid - ethyl acrylate copolymer (1:1) | 18.750 |
| Silica, colloidal anhydrous | 1.875 |
| Magnesium stearate | 5.625 |
| 1$^{st}$ layer | 375.000 |
| Flibanserin micronised | 25.000 |
| Lactose fine sieved | 71.720 |

-continued

| Ingredient | [mg/tablet] |
|---|---|
| Microcrystalline cellulose | 23.905 |
| Hypromellose 2910 | 1.250 |
| Croscarmellose sodium | 2.500 |
| Magnesium stearate | 0.625 |
| 2$^{nd}$ layer | 125.000 |
| Total | 500.000 |

EXAMPLE 1p

| Ingredient | [mg/tablet] |
|---|---|
| Flibanserin, micronised | 75.000 |
| Hydroxypropylcellulose | 75.000 |
| Hypromellose 2208 | 37.500 |
| Microcrystalline cellulose | 123.750 |
| Succinic acid | 37.500 |
| Methacrylic acid - ethyl acrylate copolymer (1:1) | 18.750 |
| Silica, colloidal anhydrous | 1.875 |
| Magnesium stearate | 5.625 |
| 1$^{st}$ layer | 375.000 |
| Flibanserin micronised | 25.000 |
| Lactose fine sieved | 71.720 |
| Microcrystalline cellulose | 23.905 |
| Hypromellose 2910 | 1.250 |
| Croscarmellose sodium | 2.500 |
| Magnesium stearate | 0.625 |
| 2$^{nd}$ layer | 125.000 |
| Total | 500.000 |

What is claimed is:

1. A pharmaceutical extended release system for an active substance with pH-dependent water solubility, comprising:
   a) flibanserin or a pharmaceutically acceptable derivative thereof as the active substance;
   b) one or more pharmaceutically acceptable pH-dependent polymers;
   c) between 15-30% by weight of one or more pharmaceutically acceptable pH-independent polymers;
   d) one or more pharmaceutically acceptable acids; and
   e) optionally one or more additives.

2. The pharmaceutical extended release system according to claim 1, wherein at least one pharmaceutically acceptable pH-dependent polymer is acrylic acid polymerisate, methacrylic acid copolymers, alginates, carrageenans, acacia, xanthan gum, chitin derivatives, carmellose sodium, carmellose calcium, phthalate, trimellitate, shellac, or derivatives or mixtures thereof.

3. The pharmaceutical extended release system according to claim 1, wherein the pharmaceutically acceptable pH-dependent polymer(s) is(are) present in an amount of 0.25-25% by weight.

4. The pharmaceutical extended release system according to claim 1, wherein at least one pharmaceutically acceptable pH-independent polymer is alkylcelluloses; hydroxyalkyl celluloses; hydroxyalkyl alkylcelluloses; carboxyalkylcellulose esters; other natural, semi-synthetic, or synthetic di-, oligo-and polysaccharides; ammonio methacrylate copolymers; polyvinylalcohol; polyvinylpyrrolidone, copolymers of polyvinylpyrrolidone with vinyl acetate; combinations of polyvinylalcohol and polyvinylpyrrolidone; polyalkylene oxides; copolymers of ethylene oxide and propylene oxide; or derivatives or mixtures thereof.

5. The pharmaceutical extended release system according to claim 1, wherein at least one pharmaceutically acceptable acid is acetic acid, l-alanine, arginine, asparagine, aspartic acid, benzenesulphonic acid, benzoic acid, p-bromophenylsulphonic acid, camphorsulphonic acid, carbonic acid, gamma-carboxyglutamic acid, citric acid, cysteine, ethanesulphonic acid, fumaric acid, gluconic acid, glutamic acid, glutaric acid, l-glutamine, hydrobromic acid, hydrochloric acid, hydroiodic acid, isethionic acid, isoleucine, lactic acid, l-leucine, lysine, maleic acid, malic acid, malonic acid, mandelic acid, methanesulphonic acid, methionine, mucinic acid, nitric acid, ornithine, oxalic acid, pamoic acid, pantothenic acid, phosphoric acid, serine, succinic acid, sulphuric acid, tartaric acid, p-toluenesulphonic acid, tyrosine, glutamic acid, valine, or derivatives or mixtures thereof.

6. The pharmaceutical extended release system according to claim 1, wherein at least one pharmaceutically acceptable acid is succinic acid, fumaric acid, malic acid, tartaric acid, glutaric acid, or mixtures thereof.

7. The pharmaceutical extended release system according to claim 1, wherein the pharmaceutically acceptable acid(s) is(are) in solid or liquid form.

8. The pharmaceutical extended release system according to claim 1, wherein the pharmaceutically acceptable acid(s) is(are) present in an amount of 0.25- 40% by weight.

9. The pharmaceutical extended release system according to claim 1, wherein the pharmaceutical extended release system is provided in the form of a tablet or bilayer tablet.

10. The pharmaceutical extended release system according to claim 1, wherein the pharmaceutical extended release system consists of

| | |
|---|---|
| flibanserin or a pharmaceutically acceptable derivative thereof | 5-50% by weight |
| pharmaceutically acceptable pH-dependent polymer(s) | 0.25-25% by weight |
| pharmaceutically acceptable pH-independent polymer(s) | 15-30% by weight |
| pharmaceutically acceptable acid(s) | 0.25-40% by weight |
| pharmaceutically acceptable lubricant(s) | 0.1-4% by weight |
| additional additives | ad 100% by weight. |

11. The pharmaceutical extended release system according to claim 1, wherein one or more additives are present that are lubricants, glidants, agents to improve flowability, granulating agents, anti-caking agents, agglomeration inhibitors, antiadherents, anti-tacking agent, anti-sticking agent, flavors, aromatiziers, dyes or colorants, preservatives, plastizers, solubilizers, wetting agents, sweeteners, chelating agents, stabilizers, antioxidants, diluents, fillers, or mixtures thereof.

12. The pharmaceutical extended release system according to claim 11, wherein a lubricant is present in an amount of 0.1-4% by weight.

13. The pharmaceutical extended release system according to claim 11, wherein the lubricants or glidants are boric acid, cellulose, silicon dioxide, glyceride, stearic acid or salts thereof, DL-leucine, magnesium silicate, calcium silicate, magnesium trisilicate, talc, starch, tribasic calcium phosphate, magnesium oxide, mineral oil, poloxamer, polyvinyl alcohol, hydrogenated oils, kaolin, mineral oil, light mineral oil, canola oil, triglycerides, myristic acid, palmitic acid, polyethylene glycols, tribasic calcium phosphate, benzoate, sodium chloride, sodium lauryl sulfate, magnesium lauryl sulphate, sodium acetate, fumaric acid and fumarate, sodium oleate, waxes or derivatives or mixtures thereof.

14. The pharmaceutical extended release system according to claim 13, wherein the lubricant or glidant is stearic acid or salts thereof, polyethylene glycol, fumaric acid, glyceride or derivatives or mixtures thereof.

15. The pharmaceutical extended release system according to claim 13, wherein the lubricant or glidant is colloidal silicon dioxide, talc, or derivatives or mixtures thereof.

16. A process for preparing the pharmaceutical extended release system according to claim 1, wherein said process comprises wet granulation, direct compression or roller compaction.

17. A capsule comprising the pharmaceutical extended release system of claim 1, wherein the pharmaceutical extended release system is in the form of granules.

18. A method of treating a condition comprising administering the pharmaceutical extended release system of claim 1 to a mammal in need thereof, wherein the condition is selected from the group consisting of: affective disorders, anxiety, Hyposexual Desire Disorder, premenstrual dysphoria, premenstrual syndrome, sexual aversion disorder, sexual arousal disorder, orgasmic disorder, dyspareunia, vaginismus, non-coital sexual pain disorder, sexual dysfunction due to a general medical condition, substance-induced sexual dysfunction, psychosis, schizophrenia, personality disorders, mental organic disorders and mental disorders in childhood, aggressiveness, age associated memory impairment, neuroprotection, cerebral ischaemia of various origins, anorexia nervosa, Attention Deficit Hyperactivity Disorder (ADHD), obesity, urinary incontinence, chronic pain or Valvular Heart Disease.

19. The method according to claim 18, wherein the flibanserin is administered in a dosage range between 0.1 to 400 mg per day.

20. The method according to claim 18, wherein the pharmaceutical extended release system is administered once or twice daily consecutively over a period of time.

21. The method according to claim 18, wherein the pharmaceutical extended release system is administered in the morning and the evening consecutively over a period of time.

22. The method according to claim 18, wherein the pharmaceutical extended release system comprises 50 or 100 mg of flibanserin and is administered only once in the evening, consecutively over a period of time.

* * * * *